United States Patent [19]

Carter et al.

[11] Patent Number: 5,731,318
[45] Date of Patent: *Mar. 24, 1998

[54] BENZOMORPHAN DERIVATIVES

[75] Inventors: Adrian Carter, Bingen; Helmut Ensinger; Matthias Grauert, both of Ingelheim am Rhein; Franz Josef Kuhn, Gau-Algesheim; Herbert Merz, Ingelheim am Rhein; Enzio Mueller, Bingen/Rh.; Werner Stransky, Gau-Algesheim; Ilse Streller, Stromberg, all of Germany

[73] Assignee: Boehringer Ingelheim KG, Ingelheim am Rhein, Germany

[*] Notice: The term of this patent shall not extend beyond the expiration date of Pat. No. 5,607,941.

[21] Appl. No.: 691,220

[22] Filed: Aug. 1, 1996

Related U.S. Application Data

[62] Division of Ser. No. 463,798, Jun. 5, 1995, Pat. No. 5,607, 941, which is a continuation of Ser. No. 217,540, Mar. 24, 1994, abandoned, which is a continuation of Ser. No. 904,738, Jun. 26, 1992, abandoned.

[30] Foreign Application Priority Data

Jul. 2, 1991 [DE] Germany ................... 412821.3

[51] Int. Cl.$^6$ .................... A61K 31/44; C07D 221/12
[52] U.S. Cl. .................... 514/289; 514/295; 546/97
[58] Field of Search ............... 546/97; 514/289, 514/295

[56] References Cited

U.S. PATENT DOCUMENTS

| | | | |
|---|---|---|---|
| 4,293,556 | 10/1981 | Merz et al. | 514/295 |
| 5,607,941 | 3/1997 | Merz et al. | 514/289 |

*Primary Examiner*—Alan L. Rotman
*Attorney, Agent, or Firm*—R. P. Raymond; M-E. M. Devlin; A. R. Stempel

[57] ABSTRACT

Novel benzomorphan derivatives of the formula

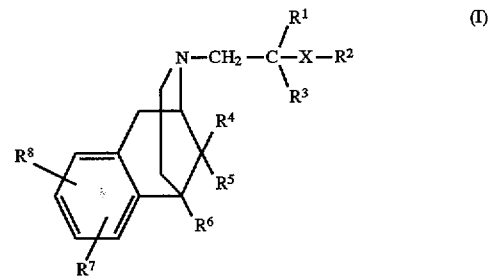

(I)

wherein $R^1$–$R^8$ are as defined herein. The benzomorphan derivatives are useful for treating cerebral ischaemia of various origins, epilepsy and neurodegenerative diseases.

5 Claims, No Drawings

BENZOMORPHAN DERIVATIVES

CROSS-REFERENCE

This application is a Division of Ser. No. 08/463,798 filed Jun. 5, 1995, now U.S. Pat. No. 5,607,941 which is a continuation of Ser. No. 08/217,540 filed Mar. 24, 1994 (Abandoned) which is a continuation of Ser. No. 07/904,738 filed Jun. 26, 1992 (Abandoned).

FIELD OF THE INVENTION

The invention relates to new benzomorphans, processes for preparing them and their use as pharmaceutical compositions.

DESCRIPTION OF THE INVENTION

The benzomorphans according to the invention correspond to general formula I:

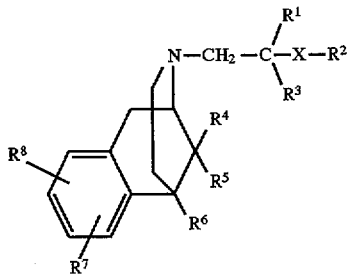

(I)

wherein

X denotes oxygen or sulphur;

$R^1$ denotes $C_{1-8}$-alkyl, $C_{3-6}$-alkenyl, $C_{3-6}$-alkynyl, aryl;

$R^2$ denotes hydrogen, $C_{1-8}$-alkyl, $C_{3-6}$-alkenyl, $C_{3-6}$-alkynyl, aryl, aralkyl;

$R^3$ denotes hydrogen, $C_{1-6}$-alkyl;

$R^4$ denotes $C_{1-8}$-alkyl;

$R^5$ denotes $C_{1-8}$-alkyl;

$R^6$ denotes $C_{1-8}$-alkyl, aryl;

$R^7$ and $R^8$ independently of each other represent hydrogen, $C_{1-8}$-alkyl, halogen, —OH, $C_{1-8}$-alkoxy, —O-acyl, —CN, —NO$_2$, NH$_2$, —NH($C_{1-8}$-alkyl), —N($C_{1-8}$-alkyl)$_2$, wherein the alkyl groups may be identical or different, —NH-acyl or —N-acyl-($C_{1-8}$-alkyl).

Preferred are compounds of general formula I wherein

X denotes oxygen or sulphur;

denotes methyl, ethyl, propyl, isopropyl, phenyl;

$R^2$ denotes methyl, ethyl, propyl, isopropyl, allyl, propargyl, phenyl, benzyl;

$R^3$ denotes hydrogen, $C_{1-4}$-alkyl;

$R^4$ denotes methyl, ethyl, propyl, isopropyl;

$R^5$ denotes methyl, ethyl, propyl, isopropyl;

$R^6$ denotes methyl, ethyl, propyl, isopropyl, phenyl;

$R^7$ denotes fluorine, chlorine, hydroxy, lower alkyl, lower alkoxy, acyloxy;

$R^8$ denotes hydrogen, lower alkyl, hydroxy or alkoxy.

Particularly preferred are compounds of general formula I wherein

X denotes oxygen;

$R^1$ denotes methyl, ethyl;

$R^2$ denotes methyl, ethyl;

$R^3$ denotes hydrogen;

$R^4$ denotes methyl, ethyl;

$R^5$ denotes methyl, ethyl;

$R^6$ denotes methyl, ethyl;

$R^7$ denotes hydroxy, methyl, methoxy, acyloxy;

$R^8$ denotes hydrogen, methyl, ethyl, hydroxy or lower alkoxy.

Most particularly preferred are compounds of general formula wherein

X denotes oxygen;

$R^1$ denotes methyl;

$R^2$ denotes methyl;

$R^3$ denotes hydrogen;

$R^4$ denotes methyl;

$R^5$ denotes methyl;

$R^6$ denotes methyl;

$R^7$ denotes hydroxy, methyl, methoxy, acetoxy; and $R^8$ denotes hydrogen, methyl, hydroxy, methoxy or ethoxy, whilst the substituents $R^7$ and $R^8$ are in the 2'-position and in the 3'-position and the 2"-carbon atom has the R-configuration.

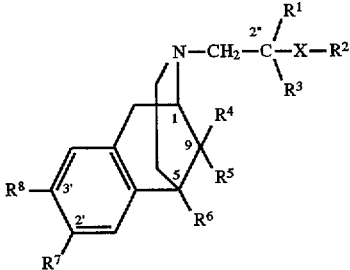

The invention relates to the individual isomers, mixtures thereof and the corresponding physiologically suitable acid addition salts with inorganic or organic acids. Examples of preferred salts are those with hydrochloric acid, hydrobromic acid, sulphuric acid, phosphoric acid, methanesulphonic acid, ethanesulphonic acid, toluenesulphonic acid, benzenesulphonic acid, lactic acid, malonic acid, succini acid, maleic acid, fumaric acid, malic acid, tartaric acid, citric acid or benzoic acid.

Unless specifically stated otherwise, the general definitions are used in the following sense:

$C_{1-6}$-alkyl or $C_{1-8}$-alkyl generally represents a straight-chained or branched hydrocarbon radical having 1 to 6 or 8 carbon atoms which may optionally be substituted by one or more halogen atoms—preferably fluorine—which may be identical to one another or different. The following hydrocarbon radicals may be mentioned by way of example: methyl, ethyl, propyl, 1-methylethyl (isopropyl), butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise stated, lower alkyl groups having 1 to 3 carbon atoms such as methyl, ethyl, propyl or isopropyl are preferred.

Alkenyl in general represents a straight-chained or branched hydrocarbon radical having 3 to 6 carbon atoms and one or more, preferably one double bond which may optionally be substituted by one halogen atom or several halogen atoms, preferably fluorine, which may be identical to one another or different.

Examples include:
2-propenyl (allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl.

The allyl group is preferred.

Alkynyl in general represents a straight-chained or branched hydrocarbon radical having 3 to 6 carbon atoms and one or more triple bonds.

A lower alkynyl radical (propargyl) having 3 carbon atoms and a triple bond which may optionally be substituted by a halogen atom—preferably fluorine—or several halogen atoms which may be identical to one another or different is preferred.

Acyl in general represents benzoyl or alkylcarbonyl radicals—such as straight-chained or branched lower alkyl having from 1 to about 6 carbon atoms bound via a carbonyl group, the alkyl radical optionally being substituted by one or more halogen atoms, which may be identical to one another or different. Alkyl groups having up to 4 carbon atoms are preferred. Examples include: acetyl, trifluoroacetyl, ethylcarbonyl, propylcarbonyl, isopropylcarbonyl, butylcarbonyl and isobutylcarbonyl. The acetyl group is particularly preferred.

Acyloxy denotes an acyl group bound via an oxygen atom, acyl being defined as hereinbefore.

Aryl in general represents an aromatic radical having 6 to 10 carbon atoms—also in combinations, it being possible for the aromatic ring to be substituted by one or more lower alkyl group(s), alkoxy group(s), nitro group(s), amino group(s) and/or one or more halogen atom(s)—which are identical to one another or different. The preferred aryl group is phenyl.

Aralkyl in general represents an aryl radical having 7 to 14 carbon atoms which is bonded via an alkylene chain, it being possible for the aromatic ring to be substituted by one or more lower alkyl group(s), alkoxy group(s), nitro group (s), amino group(s) and/or one or more halogen atom(s)— which are identical to one another or different. Aralkyl radicals having 1 to 6 carbon atoms in the aliphatic part and 6 to 10 carbon atoms in the aromatic part are preferred. Preferred aralkyl radicals which may be mentioned—unless otherwise stated—are: benzyl, phenethyl and phenylpropyl.

Alkoxy in general represents a straight-chain or branched hydrocarbon radical having 1 to 8 carbon atoms which is bonded via an oxygen atom. A lower alkoxy radical having 1 to 3 carbon atoms is preferred. The methoxy group is particularly preferred.

Unless otherwise stated, amino represents an $NH_2$-function which may optionally be substituted by one or two $C_{1-8}$-alkyl, aryl or aralkyl groups, either identical or different.

Alkylamino, for example, denotes methylamino, ethylamino, propylamino, 1-methylethylamino, butylamino, 1-methylpropylamino, 2-methylpropylamino or 1,1-dimethylethylamino.

Dialkylamino, for example, denotes dimethylamino, diethylamino, dipropylamino, dibutylamino, di-(1-methylethyl)amino, di-(1-methylpropyl)amino, di-2-methylpropylamino, ethylmethylamino or methylpropylamino.

Unless stated otherwise, halogen primarily represents fluorine, chlorine and bromine and, to a lesser degree, iodine.

1. Pharmacological Characterisation

It is known that after systemic administration of glutamate neurones are destroyed in mouse brains [S. M. Rothman and T. W. Olney, Trends in Neurosciences 10 (1987) 299]. This finding leads one to conclude, inter alia, that glutamate plays a part in neurodegenerative diseases [R. Schwarcz and B. Meldrum, The Lancet 11 (1985) 140].

In addition, substances such as quisqualic acid, cainic acid, ibotenic acid, glutamic acid and N-methyl-D-aspartic acid (NMDA) are known as exogenous or endogenous neurotoxins. In terms of their neurotoxicity these substances have a selective effect on individual types of cells, which means that loss of function can be induced in animals by specific brain lesions. This loss of function is comparable with that which occurs in connection with epilepsy and other neurodegenerative diseases, such as Huntington's chorea and Alzheimer's disease.

Furthermore, tests carried out in vivo and in vitro have shown that the cell damage and loss of function occurring in the brain as a result of hypoglycaemia, hypoxia, anoxia and ischaemia are due to an increased synaptic activity, the glutamatergic synapse being particularly significant. Substances and ions which inhibit the activity of the glutamate receptor and the ion channel connected to this receptor— such as competitive and non-competitive antagonists of excitatory amino acids as well as magnesium ions ($Mg^{2+}$) —protect the brain cells from hypoxic or ischaemic damage. These findings show that the glutamate receptor plays an important part in mediating ischaemic damage.

Biochemical and electrophysiological studies show that the receptor ion channel is highly sensitive to fluctuations in the magnesium concentration. If there is a fall in the magnesium concentration, spontaneous epileptic discharges are caused in the hippocampus, which can be inhibited by antagonists of excitatory amino acids.

Surprisingly, it has now been found that benzomorphans of general formula I block the NMDA-channel and have a neuroprotective activity.

The preparation of these benzomorphan derivatives is known from German Patent 21 05 743 and German Offenlegungsschrift 28 28 039 and from the literature [H. Merz and K. Stockhaus, J. Med. Chem. 22 (1979) 1475]. It is also already known that compounds of this kind have an analgesic effect and can be used therapeutically as non-addictive analgesics as well as antitussives (German Patent 21 05 743).

The hippocampal section is used as a test system for demonstrating the NMDA-antagonistic activity of benzomorphan derivatives. The Schäffer collaterals of the hippocampal section in an infusion chamber are stimulated by means of microelectrodes and the total potentials occurring are derived extracellularly at the pyramidal cells of the CAI-region [H. L. Haas, Schaerer and M. Vosmansky, J. Neuroscience Meth. 1 (1979) 323]. The neuroprotective effect of the benzomorphan derivatives which fall within the scope of general formula I was also demonstrated in relation to protein synthesis and the liberation of neurotransmitters in the hippocampal section.

Receptor binding tests also show that the benzomorphan derivatives disclosed are non-competitive glutamate receptor antagonists.

Furthermore, the neuroprotective activity of the benzomorphan derivatives of general formula I was tested on the mouse—in vivo—by inhibiting the lethality induced by N-methyl-D-aspartic acid [J. D. Leander et al., Brain Research 448 (1988) 115] and by inhibiting the ischaemia-induced neuronal cell death in the mouse and gerbil.

These results offer proof of the fact that the benzomorphan derivatives of general formula I can be used in neurodegenerative diseases and cerebral ischaemia of various origins. These include, for example: the epileptic state, hypoglycaemia, hypoxia, anoxia, brain trauma, brain oedema, amyotropic lateral sclerosis, Huntington's disease, Alzheimer's disease, hypotonia, cardiac infarct, cerebral stroke and perinatal asphyxia.

2. Formulation

The benzomorphan derivatives of general formula I and the acid addition salts thereof with pharmacologically acceptable acids may be converted in known manner into the usual formulations such as plain or coated tablets, pills, granules, aerosols, syrups, emulsions, suspensions and solutions, using inert pharmaceutically acceptable carriers or solvents. The proportion of pharmaceutically active compounds should be within the range from 0.5 to 90 wt.-% of the total composition, i.e. in amounts which are sufficient to achieve the dosage range specified below.

The formulations are prepared, for example, by diluting the active substances with solvents and/or carriers, optionally using emulsifiers and/or dispersing agents, whilst if water is used as the diluent, for example, organic solvents may be used as solubilisers or auxiliary solvents.

Examples of excipients include water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as natural mineral powders (e.g. kaolins, clays, talc, chalk), synthetic mineral powders (e.g. highly dispersed silica and silicates), sugars (e.g. glucose, lactose and fructose), emulsifiers (e.g. lignin, sulphite waste lyse, methylcellulose, starch and polyvinylpyrrolidone) and lubricants (e.g. magnesium stearate, talc, stearic acid and sodium laurylsulphate).

The preparations are administered in conventional manner, preferably by parenteral route, particularly by infusion, and intravenously. In the case of oral administration the tablets may, of course, contain in addition to the above-mentioned carriers additives such as sodium citrate, calcium carbonate and dicalcium phosphate together with various additional substances such as starch, preferably potato starch, gelatine and the like. In addition, lubricants such as magnesium stearate, sodium laurylsulphate and talc may be used in making the tablets. In the case of aqueous suspensions, the active substances may be combined with various flavour improvers or colourings in addition to the excipients mentioned above.

For parenteral administration, solutions of the active substances may be prepared, using suitable liquid carriers.

The dosage for oral use is from 1 to 300 mg, preferably between 5 and 150 mg.

However, it may in some cases be necessary to deviate from the amounts specified, depending on the body weight or method of administration, the individual response to the drug, the type of formulation and the time or period of time over which the preparation is administered. Thus, in some cases, it may be sufficient to use less than the prescribed minimum whereas in other cases the upper limit must be exceeded. If larger quantities are administered it may be advisable to divide them into several smaller doses distributed over the day.

Furthermore, the compounds of general formula I or the acid addition salts thereof may also be combined with active substances of other kinds.

Examples of formulations

Tablets

1. The tablet contains the following ingredients:

| | |
|---|---|
| Active substance according to formula I | 0.020 parts |
| Stearic acid | 0.010 parts |
| Dextrose | 1.890 parts |
| Total | 1.920 parts |

Preparation

The substances are mixed together in known manner and the mixture is compressed to form tablets, each weighing 1.92 g and containing 20 mg of active substance.

Ampoule solution

| Composition | |
|---|---|
| Active substance according to formula I | 1.0 mg |
| Sodium chloride | 45.0 mg |
| Water for injection | to 5.0 ml |

Preparation

The active substance is dissolved in water at its own pH or possibly at pH 5.5 to 6.5 and sodium chloride is added to make the solution isotonic. The resulting solution is filtered free from pyrogens and the filtrate is transferred under aseptic conditions into ampoules which are then sterilised and sealed by fusion. The ampoules contain 1 mg, 5 mg and 10 mg of active substance.

Suppositories

Each suppository contains:

| | |
|---|---|
| Active substance according to formula I | 1.0 parts |
| Cocoa butter (melting point: 36–37° C.) | 1200.0 parts |
| Carnauba wax | 5.0 parts |

Preparation

The cocoa butter and carnauba wax are melted together. At 45° C. the active substance is added and the mixture is stirred until fully dispersed. The mixture is poured into suitably sized moulds and the suppositories are suitably packaged.

3. Methods of synthesis

The type 2 benzomorphan derivatives used as starting material in the various methods of synthesis are either prepared according to the prior art [DE-A 20 27 077, CA 74 (1971) 125482x; EP-B 4960, CA 93 (1980) 4941 f] or are prepared as described in the following Examples.

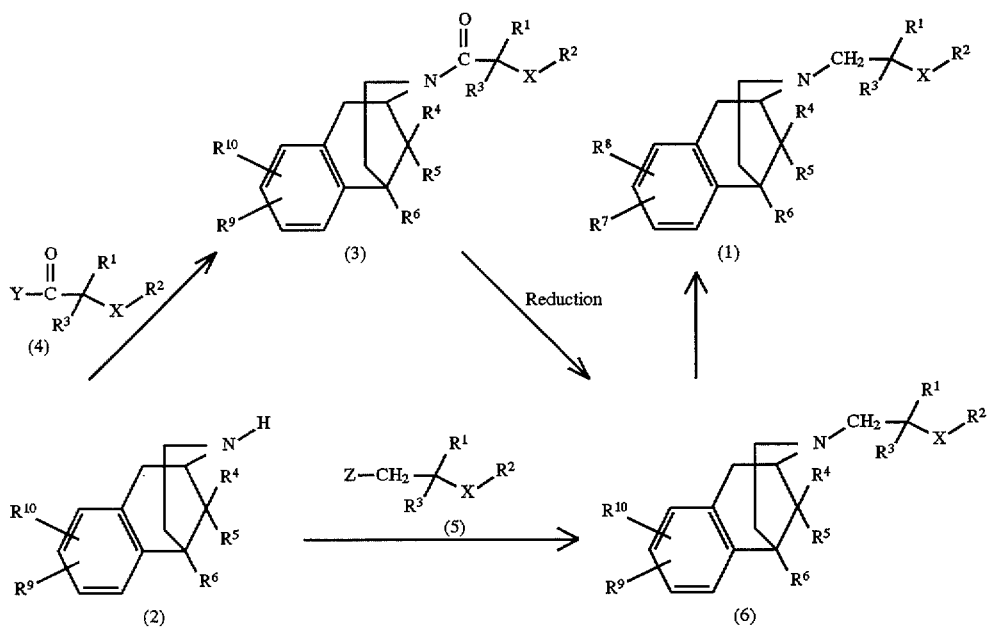

The substituents $R^9$ and $R^{10}$ are either identical to the desired substituents $R^7$ and $R^8$ or are converted into them in a later stage of synthesis.

3.1a

One way of introducing a desired substituent at the amino function of the benzomorphan nitrogen is to carry out acylation with a suitably activated carboxylic acid derivative. Corresponding carboxylic acid derivatives of type 4 are known from the prior art or are easily obtainable by current methods of synthesis.

For the acylation itself there are again a number of methods to choose from [C. Ferri, Reaktionen der organischen Synthese, Georg Thieme Verlag Stuttgart, 1978, p. 222 ff. and loc. cit. J. March, Advanced Organic Chemistry, 3rd Ed., John Wiley and Sons, New York 1985, p. 370 ff and loc. cit.; R. C. Larock, Comprehensive Organic Transformations—A Guide to Functional Group Preparations, VCH Verlagsgesellschaft, D-6940 Weinheim 1989, p. 963 ff and loc. cit.], the preferred method being reactions with carboxylic acid halides [A. L. J. Beckwith in J. Zabicki, "The Chemistry of Amides", Interscience, New York 1970 p. 73] in a solvent which is substantially inert under the reaction conditions prevailing, optionally in the presence of acid-binding agents. The inert solvents used are generally organic solvents which do not change under the reaction conditions used, such as hydrocarbons—e.g. benzene, toluene or xylene—or petroleum fractions or ethers—e.g. diethylether, glycoldimethylether (glyme), diglycoldimethylether—or cyclic ethers—e.g. tetrahydrofuran or dioxane—or halohydrocarbon—e.g. carbon tetrachloride, chloroform or dichloromethane.

The preparation of the desired carboxylic acid halides is known from the prior art [Houben-Weyl, Methoden der organischen Chemie, Volume VIII and Volume E5, Georg Thieme Verlag, Stuttgart, 1952 and 1985] where they are not commercially obtainable. Conveniently, the benzomorphan derivative of type 2 is preferably reacted in halogenated hydrocarbons, especially in dichloromethane, and in the presence of tertiary amines, such as triethylamine, with the desired acid halide, more especially with the desired acid chloride. However, it is also possible to carry out the reaction—according to the so-called Schotten-Baumann Variant—in water or in an aqueous alcohol in the presence of alkali metal hydroxides or alkali metal carbonates [see for example Organikum, Autorenkollektiv, VEB Deutscher Verlag der Wissenschaften, 17th Edition, Berlin 1988 p. 407]. Depending on the educts used it has also proved particularly advantageous to carry out the acylation according to the Einhorn variant, in which pyridine is used both as an acid-binding agent and as a reaction medium.

In addition, there is the possibility of carrying out the reaction of acylation with the free carboxylic acid [see for example A. L. J. Beckwith in J. Zabicki, "The Chemistry of hides", Interscience, New York 1970, p. 105 ff; J. A. Mitchell and E. E. Reid, J. Am. Chem. Soc. 53 (1931) 1879]. It may also prove appropriate to use a mixed anhydride, e.g. with a carbonic acid ester, instead of the free carboxylic acid [C. Ferri, Reaktionen der organischen Synhtese, Georg Thieme Verlag, Stuttgart 1978, p. 222 and loc. cit.; A. L. J. Beckwith in J. Zabicki, "The Chemistry of Amides", Interscience, New York 1970, p. 86; J. March, Advanced Organic Chemistry, 3rd Ed., John Wiley and Sons, New York 1985, p. 371 and loc. cit., R. C. Larock, Comprehensive Organic Transformations, VCH Publishers, D-6940 Weinheim 1989, p. 981 and loc. cit.].

In the preferred acylation with carboxylic acid halides, especially carboxylic acid chlorides, the reaction temperature may vary within wide limits, the lower limit being set by excessively slow reaction speeds whilst the upper limit is set by the proliferation of undesirable secondary reactions. Reaction temperatures in the range from −50° C. to 150° C., preferably from 0° C. to 75° C., have proved suitable. The work is conveniently done with a slight excess of the acylating agent in the presence of an acid binding agent (present in a somewhat larger excess) to ensure that the educts are reacted as completely as possible.

3.1b

In order to obtain the desired amine of type 6, it is necessary to reduce the acid amide 3 in the subsequent reaction step.

Reductions of acid amides of this kind are known from the prior art and may be carried out by electrolytic reduction, by reduction with alkali metals and by catalytic reduction [R. Schröter in Houben-Weyl, Methoden der organischen Chemie, Volume XI/1, Georg Thieme Verlag, Stuttgart 1957, p. 574] or with diborane or borane derivatives [J. Fuhrhop and G. Penzlin, Organic Synthesis—Concepts—Methods— Starting Materials, VCH-Verlagsgesellschaft, Weinheim 1986, p. 90].

It is preferred to carry out the reduction with complex hydrides such as alkali metal borohydrides or alkali aluminium hydrides with suitable derivatives thereof, optionally in the presence of a catalyst [N. G. Gaylord, Reduction with Complex Metal Hydrides, Wiley New York 1965; A. H àjos, Complex Hydrides, Elsevier New York 1979; V. Bažant, M. Čapka, M. Černy, V. Chvalovsky, K. Kochloefl, M. Kraus und J. Màlek, Tetrahedron Lett. 9-(1968) 3303], lithium aluminium hydride being particularly preferred.

Suitable reaction media are all the inert organic solvents which do not change under the reaction conditions specified. These preferably include ethers such as diethylether, diisopropylether, tert.-butylmethylether, di-n-butylether, glycoldimethylether (glyme), diglycoldimethylether (diglyme), cyclic ethers such as dioxane and, particularly preferably, tetrahydrofuran, the choice of solvent being guided, inter alia, by the particular reducing agent used.

It is generally advantageous to allow these reductions to proceed in the presence of an excess of the reducing agent, which preferably takes the form of one of the abovementioned complex hydrides, particularly lithium alanate, in a range from 5 to 100%, preferably in the range from 10 to 50%.

The reactants are usually added whilst cooling with ice or at ambient temperature and then heated to temperatures in the region of 150° C., preferably up to 75° C., depending on the reactivity of the educts.

3.2

Another possible method of preparing benzomorphan derivatives of type 6 is to react the benzomorphan derivative 2 with suitable alkylating agents of type 5, in which Z in formula 5 represents a leaving group which leaves during the alkylation. Preferred leaving groups are halogen, such Cl, Br and I, or O—$SO_2$-aryl, such tosylate, or an alkylsulphonate O—$SO_2$-alkyl, such as methanesulphonate or halomethanesulphonate or sulphate. Corresponding alkylating reagents are either commercially obtainable or may be prepared by methods known in the art.

Suitable solvents include all inert solvents which remain substantially unchanged under the reaction conditions specified and which, because they are not themselves reactive components, cannot have a negative influence on the course of the reaction. Examples are alcohols, such methanol, ethanol, propanol or isopropanol, or ethers, such as diethylether, di-n-butyl-ether, tert.butylmethylether, glycoldimethylether (glyme), diethyleneglycoldimethylether (diglyme), tetrahydrofuran and dioxane—or ketones, such as methylethyl ketone acetone, or acid amides, such as hexane-methylphosphoric acid triamide or dimethylformamide.

It is also possible to use mixtures of the abovementioned solvents. Tetrahydrofuran or dimethylformamide or mixtures of these two solvents are particularly preferred. The reaction is preferably carried out in the presence of acid-binding agents such as alkali or alkaline earth metal carbonates or hydrogen carbonates.

The reaction temperature may vary within wide limits in the course of the reaction, these limits being set by too slow a reaction rate, at the bottom of the scale, for practical purposes, and by a prevalence of side reactions, at the top of the scale. Suitable reaction temperatures fall within the range from 0° C. to 150° C. and preferably from 50° C. to 100° C.

3.3

The conversion of $R^9$ and/or $R^{10}$ into $R^7$ and $R^8$, respectively, which may be necessary, involves a number of different reactions, which cannot be combined under a single plan. Such conversion reactions are described in the corresponding Examples.

4. EXAMPLES

Preliminary remark: Unless otherwise stated, the word ether denotes diethylether.

4.1 Compounds of type (1)—prepared according to process 3.1

4.1.1 Example 1

(−)-(1R,5S,2"R)-2'-hydroxy-2-(2-methoxy-propyl)-
5,9,9-trimethyl-6,7-benzomorphan hydrochloride a) Acylation 27.8 g (0.12 mol) of (±)-2'-hydroxy-5,9,9-trimethyl-6,7-benzomorphan [DOS 20 27 077; CA 74, 125482x (1971)] are mixed with 278 ml of absolute dichloromethane in the presence of 27.9 g (0.275 mol) of triethylamine and 19.2 g (0.156 mol) of (R)-2-methoxypropionic acid chloride are added, with stirring, within about 30 minutes. The reaction temperature is maintained in the range from 30° to 35° C. The mixture is then refluxed for one hour. It is then cooled and washed successively with 175 ml of water, 1.75 ml of 2N hydrochloric acid and twice more with 175 ml of water. After drying with sodium sulphate and filtering off the drying agent the solution is evaporated down in vacuo, at a final temperature of 80° C. under a full water jet vacuum. The acylation product of type (3) is obtained As an evaporation residue in a yield of 42.3 g (around 100% of theory).

b) Reduction

The acylation product prepared using the process described above is dissolved in 425 ml of absolute tetrahydrofuran. The solution is added dropwise, with stirring and cooling with ice, to a suspension of 9.1 g (0.24 mol) of lithium aluminium hydride (lithium tetrahydridoalanate) in 300 ml of tetrahydrofuran within one hour at 10° to 15° C. Then the reaction mixture is refluxed for two hours with stirring. 25 ml of water are then added dropwise thereto, whilst cooling in an ice bath and with stirring, and finally, after the addition of a further 70 ml of water and saturated diammonium tartrate solution (890 ml), the mixture is shaken in a separating funnel. The tetrahydrofuran phase separated off is evaporated down in vacuo and the aqueous phase is extracted three times with 175 ml of dichloromethane. The evaporation residue of the tetrahydrofuran phase is dissolved with the dichloromethane extracts and the solution is washed twice with 100 ml of water. After drying with sodium sulphate and removal of the drying agent by filtering, the solution is evaporated down, at a final temperature of 80° C. under a full water jet vacuum. A residue remains (37 g, about 100% of theory), which consists of a mixture of the two diastereomeric compounds expected. In the thin layer chromatograph (TLC) these diastereomers show $R_f$ values of 0.42 and 0.51 (silica gel 60, chloroform-methanol-conc. ammonia 95:5:0.1).

The diastereomers can be separated by crystallisation of the hydrochlorides. To do this, the basic mixture is dissolved in 120 ml of absolute ethanol and the solution is acidified with hydrochloric acid (12 ml 32% hydrochloric acid). The title compound ($R_f$=0.42) crystallises immediately, is cooled (ice bath), suction filtered, washed with ice cold ethanol (40 ml) in batches and is dried, at a final temperature of 80° C., until a constant weight is achieved. The yield is 15.0 g (73.5% of the maximum amount theoretically obtainable). The substance melts at 264° C. with decomposition and has a specific optical rotation of $[\alpha]_D^{25}=-116.9°$ (c=1, CH$_3$OH). A sample recrystallised from a mixture of methanol and diethylether melts at an uncharged melting point of 264° C. (decomp.) and has a specific rotation of $[\alpha]_D^{25}=-118.6°$ (c=1, CH$_3$OH).

4.1.2 Example 2

(+)-(1S,5R,2"R)-2'-hydroxy-2-(2-methoxy-propyl)-5,9,9-trimethyl-6,7-benzomorphan hydrochloride The mother liquor obtained in the process according to Example 1 contains predominantly the diastereomer with an R$_f$ value of 0.51. It is evaporated down and the residue (25 g) is heated to reflux temperature with 40 ml of isopropanol for one hour with stirring. The crystal suspension thus obtained is left to stand at ambient temperature for about 12 hours, then suction filtered and washed in batches with a little cold isopropanol. The crystals consist mainly of the title compound together with residues of the diastereomer (Example 1). The title compound is converted into the free base form and purified by column chromatography. For this purpose, the crystals are shaken with water (75 ml), dichloromethane (75 ml) and excess conc. ammonia (25% strength, 6 ml). After separation of the phases the aqueous layer is extracted once more with 25 ml of dichloromethane. The combined dichloromethane extracts are washed twice with 25 ml of water, then dried with sodium sulphate and, after removal of the drying agent by filtration, evaporated down at a final temperature of 80° C. under a full water jet vacuum. The residue (15.4 g) is purified by column chromatography on 2 kg of silica gel (MN K 60, 230–400 mesh ASTM made by Macherey and Nagel) using dichloromethane-methanol-conc. ammonia 95:5:0.1 as eluant. The fractions containing the pure substance yield a residue (6.8 g) after evaporation, consisting of the base of the title compound. The residue is dissolved with 14 ml of absolute ethanol and the solution is acidified with 10 ml of 2.5N ethanolic hydrochloric acid. After the addition of diethylether until the turbidity is just constant, the title compound crystallises out. The mixture is left to stand in the refrigerator for about 12 hours and then suction filtered and washed first with an methanol-ether mixture 1:2 and then with ether. After drying, finally at 80° C., 6.4 g of the title compound are obtained (31.4% of the maximum amount theoretically obtainable) with a melting point of 236° C. (decomp.) and a specific rotation of $[\alpha]_D^{25}=+88.0°$ (c=1, CH$_3$OH)

4.1.3 Example 3

(+)-(1S,5R,2"S)-2'-hydroxy-2-(2-methoxy-propyl)-5,9,9-trimethyl-6,7-benzomorphan hydrochloride Starting from 9.25 g (0.040 mol) of (±)-2'-hydroxy-5,9,9-trimethyl-6,7-benzomorphan and 6.37 g (0.052 mol) of (S)-2-methoxypropionic acid chloride, the title compound is obtained analogously to Example 1 in a yield of 5.1 g (75.0% of theory) with an R$_f$ value of 0.42, a melting point of 270° C. (decomp.) and a specific rotation of $[\alpha]_D^{25}=+117°$ (c=1, CH$_3$OH).

4.1.4 Example 4

(−)-(1R,5S,2"S)-2'-hydroxy-2-(2-methoxy-propyl)-5,9,9-trimethyl-6,7-benzomorphan hydrochloride Starting from the mother liquor obtained in Example 3 the title compound is obtained analogously to Example 2 in a yield of 3.2 g (47.1% of theory) with a melting point of 235° C. (decomp.) and a specific rotation of $[\alpha]_D^{25}=-89.9°$ (c=1, CH$_3$OH).

4.1.5 Example 5

(−)-(1R,5S,2"R)-2'-hydroxy-2-(2-methoxy-propyl)-5,9,9-trimethyl-6,7-benzomorphan hydrochloride If instead of the racemic starting compound 2.31 g (0.010 mol) of the enantiomerically pure (−)-2'-hydroxy-5,9,9-trimethyl-6,7-benzomorphan are reacted analogously to Example 1 with 1.60 g (0.013 mol) of (R)-2-methoxypropionic acid chloride, instead of a mixture of the diastereomeric bases the sterically pure base of the title compound will first be obtained and from this the hydrochloride is obtained in a yield of 3.0 g (88.4% of theory) with a melting point of 264° C. (decomp.) and a specific rotation of $[\alpha]_D^{20}=-117.5°$ (c=1, CH$_3$OH).

4.1.6 Example 6

(−)-(1R,5S,2"S)-2'-hydroxy-2-(2-methoxy-propyl)-5,9,9-trimethyl-6,7-benzomorphan hydrochloride If the synthesis described in Example 5 is carried out with (S)-2-methoxypropionic acid, the title compound is obtained in a yield of 2.9 g (85.3% of theory) with a melting point of 235° C. (decomp.) and a specific rotation of $[\alpha]_D^{25}=-89.7°$ (c=1, CH$_3$OH).

4.1.7 Example 7

(−)-(1R,5S,2"R)-2'-hydroxy-2-(2-methoxy-propyl)-5,9,9-trimethyl-6,7-benzomorphan hydrochloride Starting from 4.62 g (0.020 mol) of (−)-2'-hydroxy-5,9,9-trimethyl-6,7-benzomorphan and 3.20 g (0.026 mol) of (R/S)-2-methoxypropionic acid chloride, there is obtained analogously to Example 1 a mixture of the expected diastereomeric bases which are separated by column chromatography analogously to Example 2. The slower running substance (R$_f$=0.42) is crystallised as the hydrochloride as described therein. The title compound is obtained in a yield of 2.1 g (61.8% of theory) with a melting point of 264° C. (decomp.) and a specific rotation of $[\alpha]_D^{25}=31\ 117.9°$ (c=1, CH$_3$OH).

4.1.8 Example 8

(−)-(1R,2S,2"S)-2'-hydroxy-2-(2-methoxy-propyl)-5,9,9-trimethyl-6,7-benzomorphan hydrochloride Starting from the faster running substance (R$_f$=0.51) separated in Example 7, the title compound is obtained, after conversion into the hydrochloride analogously to Example 2, in a yield of 2.2 g (64.7% of theory) with a melting point of 235° C. (decomp.) and a specific rotation of $[\alpha]_D^{25}=-88.6°$ C. (c=1, CH$_3$OH).

4.1.9 Example 9

(+)-(1S,5R,2"S)-2'-hydroxy-2-(2-methoxy-propyl)-5,9,9-trimethyl-6,7-benzomorphan hydrochloride 2.60 g (0.025 mol) of (S)-2-methoxypropionic acid chloride are stirred in 100 ml of absolute tetrahydrofuran with 4.04 g (0.025 mol) of 1,1'-carbonyldiimidazole for two hours at ambient temperature. After the addition of 4.62 g (0.020 mol) of (+)-2'-hydroxy-5,9,9-trimethyl-6,7- benzomorphan the mixture is stirred for a further two days at ambient temperature. It is then evaporated down, the residue is taken up in 75 ml of dichloromethane and washed successively with 2N HCl and twice with water. After separation the organic phase is dried with sodium sulphate and after the drying agent has been filtered off, the residue is evaporated down in vacuo, finally at 80° C. under a full water jet vacuum. The evaporation residue is reduced with lithium aluminium hydride (lithium tetrahydridoalanate) as described in Example 1 and the reaction product is crystallised as the hydrochloride analogously to Example 2. The title compound is obtained in a yield of 6.9 g (81.3% of theory) with a melting point of 264° C. (decomp.) and a specific rotation of $[\alpha]_D^{25}$=+117.4° (c=1, CH$_3$OH).

4.1.10 Example 10

(−)-(1R,5S,2"R)-9,9-dimethyl-5-ethyl-2'-hydroxy-2-(2-methoxypropyl)-6,7-benzomorphan hydrochloride Starting from 1.69 g (0.006 mol) of (±)-9,9-dimethyl-5-ethyl-2"-hydroxy-6,7-benzomorphan hydrochloride [DOS 20 27 077; CA 74, 125482x (1971)], 1.82 g (0.018 mol) of triethylamine and 0.96 g (0.0078 mol) of (R)-2-methoxypropionic acid chloride, a mixture of the expected diastereomeric bases (1.7 g) is obtained analogously to Example 1, these bases being separated by column chromatography analogously to Example 2. The slower running substance (0.6 g, $R_f$=0.40) is crystallised out as the hydrochloride analogously to Example 2. The title compound is obtained in a yield of 0.6 g (56.6% of theory) with a melting point of 275° C. (decomp.) and a specific rotation of $[\alpha]_D^{25}$=−100.5° (c=1, CH$_3$OH).

4.1.11 Example 11

(+)-(1S,5R,2"R)-9,9-dimethyl-5-ethyl-2'-hydroxy-2-(2-methoxypropyl)-6,7-benzomorphan hydrochloride The faster running diastereomer (0.7 g, $R_f$=0.45) separated by column chromatography in Example 10 is crystallised out as the hydrochloride analogously to Example 2. The title compound is obtained in a yield of 0.23 g (21.7% of theory) with a melting point of 216° C. (decomp.) and a specific rotation of $[\alpha]_D^{25}$=+62.4° (c=1, CH$_3$OH).

4.1.12 Example 12

(+)-(1S,5R,2"S)-9,9-dimethyl-5-ethyl-2'-hydroxy-2-(2-methoxypropyl)-6,7-benzomorphan hydrochloride Starting from 1.69 g (0.006 mol) of (±)-9,9-dimethyl-5-ethyl-2'-hydroxy-6,7-benzomorphan hydrochloride, 1.82 g (0.018 mol) of triethylamine and 0.96 g (0.0078 mol) of (S)-2-methoxypropionic acid chloride, a mixture of the expected diastereomeric bases (1.7 g) is obtained analogously to Example 1 and separated by column chromatography analogously to Example 2. The slower running substance (0.6 g, $R_f$=0.40) is crystallised out as the hydrochloride analogously to Example 2. The title compound is obtained in a yield of 0.6 g (56.6% of theory) with a melting point of 275° C. (decomp) and a specific rotation of $[\alpha]_D^{25}$=+102.5° (c=1, CH$_3$OH).

4.1.13 Example 13

(−)-(1R,5S,2"S)-9,9-dimethyl-5-ethyl-2'-hydroxy-2-(2-methoxypropyl)-6,7-benzomorphan hydrochloride The faster running diastereomer (0.6 g, $R_f$=0.45) separated by column chromatography according to Example 12 is crystallised out as the hydrochloride analogously to Example 2. The title compound is obtained in a yield of 0.65 g (61.2% of theory) with a melting point of 219° C. (decomp.) and a specific rotation of $[\alpha]_D^{25}$=−67.6° (c=1, CH$_3$OH)

4.1.14 Example 14

(−)-9,9-dimethyl-2'-hydroxy-2-((R)-2-methoxypropyl)-5-phenyl-6,7-benzomorphan

Starting from 1.76 g (6 mMol) of (±)-9,9-dimethyl-2'-hydroxy-5-phenyl-6,7-benzomorphan [EP-B-4960; CA 93, 4941f (1980)] and 0.96 g (7.8 mMol) of (R)-2-methoxypropionic acid chloride, a mixture of the expected diastereomeric bases (2.1 g) is obtained analogously to Example 1 with $R_f$-values of 0.50 and 0.55 (cf. Example 2). The mixture is crystallised out in the form of the hydrochlorides (2.4 g) analogously to Example 2 and converted back into the corresponding free bases (evaporation residue 1.8 g). This base residue is recrystallised from 6 ml of ethyl acetate and 18 ml of petroleum ether (80° C.). Then the title compound is obtained in a yield of 0.72 g (65.5% of theory) with a melting point of 202° C., an $R_f$ value of 0.50 and a specific rotation of $[\alpha]_D^{25}$=−24.4° (c=1, CH$_3$OH)

4.1.15 Example 15

(+)-9,9-dimethyl-2'-hydroxy-2-((R)-2-methoxypropyl)-5-phenyl-6,7-benzomorphan hydrochloride The mother liquor (ethyl acetate/petroleum ether) obtained during crystallisation according to Example 13 is evaporated down. The residue (1.2 g) is dissolved in 5 ml of ethanol and the solution is acidified with 2.5N ethanolic hydrochloric acid. After the addition of diethylether until turbidity is beginning, hydrochloride (0.4 g) crystallises out as a contaminated crude product. The mother liquor contains the pure title compound which, after evaporation, is isolated as a residue: yield: 0.75 g (62.0% of theory), melting point 168° C. (decomp.), $R_f$=0.55, specific rotation $[\alpha]_D^{25}$=+11.6° (c=1, CH$_3$OH)

4.1.16 Example 16

(−)-(1R,5S,2"R)-3'-hydroxy-2-(2-methoxy-propyl)-5,9,9-trimethyl-6,7-benzomorphan hydrochloride a) Starting compound The (±)-3'-hydroxy-5,9,9-trimethyl-6,7-benzomorphan required here and in other Examples is not known from the prior art. It may be prepared, for example, using the method of synthesis given for the known 2'-hydroxy-isomer [DOS 20 27 077,; CA 74, (1971), 125482x], using m-methoxybenzyllithium instead of p-methoxybenzyllithium. When cyclisation is carried out to obtain the benzomorphan system, two isomeric compounds are obtained in the latter case which are further reacted in the form of a mixture. The mixture of 1'-hydroxy- and 3'-hydroxy-5,9,9-trimethyl-6,7-benzomorphan obtained finally is separated by flash column chromatography on 100 times the quantity of silica gel (MN K 60, 230–400 mesh ASTM, made by Macherey and Nagel) using a mixture of ethyl acetate/ methanol/conc. ammonia 80:20:5 as eluant. The (±)-1'-hydroxy-5,9,9-trimethyl-6,7-benzomorphan ($R_f$=0.20) and the (±)-3'-hydroxy-5,9,9-trimethyl-6,7-benzomorphan ($R_f$=0.14) are obtained in a ratio of 1:2 in the form of viscous oils ($R_f$ values: TLC, silica gel 60, using the eluant mentioned above).

b) Reaction to obtain the title compound

Starting from 2.31 g (0.010 mol) of (±)-3'-hydroxy-5,9,9-trimethyl-6,7-benzomorphan and 1.6 g (0.013 mol) of (R)-2-methoxypropionic acid chloride, a mixture of the expected diastereomeric bases is obtained analogously to Example 1 which are separated by column chromatography on 100 times the quantity of silica gel analogously to Example 2. The slower running substance ($R_f$=0.65) is crystallised out as the hydrochloride, as described therein. The title compound is obtained in a yield of 0.86 g (50.6%) with a melting point of 240° to 242° C. (decomp.) and a specific rotation of $[\alpha]_{D25}$=−90.9° (c=1, CH$_3$OH).

4.1.17 Example 17

(+)-(1S,5R,2"R)-3'-hydroxy-2-(2-methoxy-propyl)-5,9,9-trimethyl-6,7-benzomorphan hydrochloride The faster running substance ($R_f$=0.74) separated in Example 16 is crystallised out as the hydrochloride analogously to Example 2. The title compound is obtained in a yield of 1.28 g (75.3% of theory) with a melting point of 250°–251° C. and a specific rotation of $[\alpha]_D^{25}$=+57.1° (c=1, CH$_3$OH)

4.1.18 Example 18

(+)-(1S,5R,2"S)-3'-hydroxy-2-(2-methoxy-propyl)-5,9,9-trimethyl-6,7-benzomorphan hydrochloride Starting from 2.31 g (0.010 mol) of (±)-3'-hydroxy-5,9,9-trimethyl-6,7-benzomorphan (see Example 16) and 1.60 g (0.013 mol) of (S)-2-methoxypropionic acid chloride, a mixture of the expected diastereomeric bases is obtained analogously to Example 1, which are purified by chromatography analogously to Example 2 on 100 times the amount of silica gel. The slower running substance ($R_f$=0.65) is crystallised as the hydrochloride as described therein. The title compound is obtained in a yield of 0.57 g (33.4% of theory) with a melting point of 239° to 240° C. (decomp.) and a specific rotation of $[\alpha]_D^{25}$=+90.7° (c=1, CH$_3$OH)

4.1.19 Example 19

(−)-(1R,5S,2"S)-3'-hydroxy2-(2-methoxy-propyl)5,9,9-trimethyl-6,7-benzomorphan hydrochloride The faster running substance ($R_f$=0.74) separated in Example 18 is crystallised out as the hydrochloride analogously to Example 2. The title compound is obtained in a yield of 0.67 g (39.2% of theory) with a melting point of 250°–251° C. (decomp.) and a specific rotation of $[a]_D^{25}$=−56.5° (c=1, CH$_3$OH).

4.1.20 Example 20

(−)-(1R,5R,2"R)-1'-hydroxy-2-(2-methoxy-propyl)-5,9,9-trimethyl-6,7-benzomorphan hydrochloride Starting from 2.31 g (0.010 mol) of (±)-1'-hydroxy-5,9,9-trimethyl6,7-benzomorphan (see Example 16) and 1.60 g of (R)-2-methoxypropionic acid chloride, a mixture of the expected diastereomeric bases is obtained analogously to Example 1 which are separated analogously to Example 2 on 100 times the amount of silica gel. The slower running substance ($R_f$=0.52) is crystallised as the hydrochloride analogously to Example 2. The title compound is obtained in a yield of 0.70 g (41.2% of theory) with a melting point of 128°–135° C. (decomp.) and a specific rotation of $[\alpha]_D^{25}$=−100.5° (c=1, CH$_3$OH)

4.1.21 Example 21

(+)-(1S,5S,2"R)-1'-hydroxy-2-(2-methoxy-propyl)-5,9,9-trimethyl-6,7-benzomorphan hydrochloride The faster running substance ($R_f$=0.56) separated off in Example 20 is crystallised as the hydrochloride analogously to Example 2. The title compound is obtained in a yield of 0.40 g (23.6% of theory) with a melting point of 88° to 89° C. (decomp.) and a specific rotation of $[\alpha]_D^{25}$=50.4° (c=1, CH$_3$OH).

4.1.22 Example 22

(+)-(1S,5S,2"S)-1'-hydroxy-2-(2-methoxy-propyl)-5,9,9-trimethyl-6,7-benzomorphan hydrochloride Starting from 2.31 g (0.010 mol) of (±)-1'-hydroxy-5,9,9-trimethyl-6,7-benzomorphan (see Example 16) and 1.60 g (0.013 mol) of (S)-2-methoxy-propionic acid chloride a mixture of the expected diastereomeric bases is obtained analogously to Example 1 which are separated on 100 times the amount of silica gel in accordance with Example 2. The slower running substance ($R_f$=0.52) is crystallised out as the hydrochloride analogously to Example 2. The title compound is obtained in a yield of 0.63 g (36.8% of theory) with a melting point of 85° to 90° C. and a specific rotation of $[\alpha]_D^{25}$=+96.2° (c=1, CH$_3$OH).

4.1.23 Example 23

(−)-(1R,5R,2"S)-1'-hydroxy-2-(2-methoxy-propyl)-5,9,9-trimethyl-6,7-benzomorphan hydrochloride The faster running substance ($R_f$=0.56) separated in Example 22 is crystallised as the hydrochloride analogously to Example 2. The title compound is obtained in a yield of 0.50 g (29.4% of theory) with a melting point of 90° to 91° C. (decomp.) and a specific rotation of $[\alpha]_D^{25}$=−64.0° (c=1, CH$_3$OH)

4.1.24 Example 24

(−)-(1R,5S,2"R)-4'-hydroxy-2-(2-methoxy-propyl)-5,9,9-trimethyl-6,7-benzomorphan hydrochloride a) Preparation of the starting compound The preparation of (±)-4'-hydroxy-5,9,9-trimethyl-6,7-benzomorphan needed here and in other Examples is not known from the prior art. It may, for example, be prepared by the method of synthesis known from the prior art for the known 2'-hydroxy-isomer [DOS 20 27 077, CA 74, 125482x (1971)] by using o-methoxybenzyllithium instead of p-methoxybenzyllithium. The desired compound crystallises as a base from isopropanol-petroleum ether with a melting point of 227° C. In thin layer chromatography (silica gel 60, chloroform/methanol/conc. ammonia 65:35:3) it may be given an $R_f$ value of 0.20.

b) Reaction to obtain the title compound

Starting from 2.31 g (0.010 mol) of (±)-4'-hydroxy-5,9,9-trimethyl-6,7-benzomorphan and 1.60 g (0.01 mol) of (R)-2-methoxypropionic acid chloride, a mixture of the expected bases (3.0 g) is obtained analogously to Example 1, which are separated analogously to Example 2 by column chromatography on 450 g of silica gel. 0.9 g of the slower running compound ($R_f$=0.34) and 1.3 g of the faster running compound ($R_f$=0.43) are obtained. The former is crystallised as the hydrochloride as in Example 2. The title compound is thus obtained in a yield of 0.95 g (55.9% of theory) with a melting point of 263° C. (decomp.) and the specific rotation of $[\alpha]_D^{25}$=−86.9° (c=CH$_3$OH)

4.1.25 Example 25

(+)-(1S,5R,2"R)-4'-hydroxy-2-(2-methoxy-propyl)-5,9,9-trimethyl-6,7-benzomorphan hydrochloride The faster running compound ($R_f$=0.43) separated in Example 24 is crystallised as the hydrochloride analogously to Example 2. The title compound is obtained in a yield of 1.23 g (72.4% of theory) with a melting point of 258° C. (decomp.) and a specific rotation of $[\alpha]_D^{25}$=+51.7° (c=1, CH$_3$OH).

4.1.26 Example 26

(+)-(1S,5R,2"S)-4'-hydroxy-2-(2-methoxy-propyl)-5,9,9-trimethyl-6,7-benzomorphan hydrochloride Starting from 2.31 g (0.010 mol) of (±)-4'-hydroxy-5,9,9-trimethyl-6,7-benzomorphan (see Example 24) and 1.60 g (0.013 mol) of (S)-2-methoxypropionic acid chloride, a mixture of the expected diastereomeric bases (3.1 g) is obtained which are separated by column chromatography on 450 g of silica gel analogously to Example 2. 1.0 g of the slower running compound ($R_f$=0.34) and 1.2 g of the faster running compound are obtained. The former is crystallised in the form of the hydrochloride analogously to Example 2 and yields the title compound in a yield of 1.15 g (67.7%) with a melting point of 260° C. (decomp.) and a specific rotation of $[\alpha]_D^{25}$=-51.2° (c=1, CH$_3$OH).

4.1.27 Example 27

(−)-(1R,5S,2"S)-4'-hydroxy-2-(2-methoxy-propyl)-5,9,9-trimethyl-6,7-benzomorphan hydrochloride The faster running substance ($R_f$=0.43) separated in Example 26 is crystallised as the hydrochloride analogously to Example 2 and yields the title compound in a yield of 0.95 g (55.9% of theory) with a melting point of 261° C. (decomp.) and a specific rotation of $[\alpha]_D^{25}$=+86.1° (c=1 CH$_3$OH)

4.1.28 Example 28

(−)-(1R,5S,2"R)-2'-methoxy-2-(2-methoxy-propyl)-5,9,9-trimethyl-6,7-benzomorphan methanesulphonate Starting from 2.45 g (0.010 mol) of (−)-2'-methoxy-5,9,9-trimethyl-6,7-benzomorphan [DOS 20 27 077; CA 125482x (1971)] and 1.35 g (0.011 mol) of (R)-2-methoxypropionic acid chloride, the sterically uniform title compound is obtained analogously to Example 1 in the form of the free base (2.3 g). This is dissolved in 5 ml of absolute ethanol. After acidification with methanesulphonic acid the solution obtained is combined with diethylether until turbidity is just beginning. Whilst the methanesulphonate is crystallising, the same amount of ether is gradually added once more with stirring. Then the reaction mixture is cooled for 4 hours with an ice bath, suction filtered, then washed first with a 1:2 mixture of ethanol and ether and then with ether on its own. After drying, finally at 80° C., the title compound is obtained in a yield of 3.3 g (79.8% of theory) with a melting point of 165°–166° C. (decomp.) and a specific rotation of $[\alpha]_D^{25}$=-92.4° (c=1, CH$_3$OH)

4.1.29 Example 29

(+)-(1S,5R,2"S)-2'-methoxy-2-(2-methoxy-propyl)-5,9,9-trimethyl-6,7-benzomorphan methanesulphonate Starting from 2.45 g (0.010 mol) of (+)-2'-methoxy-5,9, 9-trimethyl-6,7-benzomorphan [DOS 20 27 077; CA 74, 125482x (1971)] and 1.35 g (0.011 mol) of (S)-2-methoxypropionic acid chloride, the title compound is obtained analogously to Example 28 in a yield of 3.1 g (75.0% of theory) with a melting point of 165°–167° C. (decomp.) and a specific rotation of $[\alpha]_D^{25}$=+92.3° (c=1, CH$_3$OH).

4.1.30 Example 30

(−)-(1R,5S,2"R)-2-(2-methoxypropyl)-5,9,9-trimethyl-6,7-benzomorphan hydrochloride a) Preparation of the starting compound The preparation of (±)-5,9,9-trimethyl-6,7-benzomorphan required here and in other Examples is not known from the prior art. It may be prepared, for example, using the method of synthesis given for the known 2'-hydroxy derivative [DOS 20 27 077; CA 74 (1971) 125482x], using benzyllithium instead of p-methoxybenzyllithium. The desired compound crystallises as a hydrobromide from an isopropanol-ether mixture with a melting point of 259° C. (decomposition).

b) Reaction to obtain the title compound

Starting from 2.96 g (0.010 mol) of (±)-5,9,9-trimethyl-6,7-benzomorphan and 1.35 g (0.011 mol) of (R)-2-methoxypropionic acid chloride, a mixture of the expected diastereomeric bases is obtained analogously to Example 1. These are separated according to Example 2 by column chromatography on 150 times the amount of silica gel. The slower running substance ($R_f$=0.63) is crystallised as the hydrochloride, as described therein. The title compound is obtained in a yield of 1.3 g (76.5% of theory) with a melting point of 225° C. (decomp.) and a specific rotation of $[\alpha]_D^{25}$=-101.7° (c=1, CH$_3$OH).

4.1.31 Example 31

(+)-(1S,5R,2"R)-2-(2-methoxypropyl)-5,9,9-trimethyl-6,7-benzomorphan oxalate

The faster running substance ($R_f$=0.67) separated in Example 30 is dissolved with 5 ml of ethanol. After acidification with oxalic acid the solution is mixed with diethylether until turbidity is just beginning. During the crystallisation which then sets in, half the original quantity of ether is gradually added and the mixture is left in the refrigerator for about 12 hours. After suction filtering, washing with an ethanol-ether mixture and drying at 80° C., the title compound is obtained in a yield of 1.1 g (60.4% of theory) with a melting point of 135° C. (decomp.) and a specific rotation of $[\alpha]_D^{25}$=+60.2° (c=1, CH$_3$OH).

4.1.32 Example 32

(−)-(1R,5S,2"R)-2-(2-Methoxypropyl)-2',5,9,9-tetramethyl-6,7-benzomorphan hydrochloride a) Preparation of the starting compound The (±)-2'-5,9,9-tetramethyl-6,7-benzomorphan required here and in other Examples is not known from the prior art. It may, for example, be prepared using the method of synthesis given for the known 2'-hydroxy-analogue, using p-methylbenzyllithium instead of p-methoxybenzyllithium. The intermediate product thus obtained is crystallised in the form of the hydrobromide from an isopropyl-diethylether mixture and melts at 227° C. with decomposition.

b) Reaction to obtain the title compound

Starting from 1.51 g (5 mMol) of (±)-2'-5,9,9-tetramethyl-6,7-benzomorphan and 0.68 g (5.5 mMol) of (R)-2-methoxypropionic acid chloride, a mixture of the expected diastereomeric bases is obtained analogously to Example 1, which are crystallised as the hydrochlorides and separated as described therein. The title compound is obtained in a yield of 0.7 g (after recrystallisation 0.4 g=47.3% of theory) with a melting point of 212° C. (decomp.) and a specific rotation of $[\alpha]_D^{25}=-110.0°$ (c=1, $CH_3OH$).

4.1.33 Example 33

(+)-1S,5R,2"S)-2-(2-methoxypropyl)-2',5,9,9-trimethyl-6,7-benzomorphan hydrochloride Starting from 1.51 g (5 mMol) of (±)-2'-5,9,9-tetramethyl-6,7-benzomorphan and 0.68 g (5.5 mMol) of (S)-2-methoxypropionic acid chloride the title compound is obtained analogously to Example 32 in a yield of 0.4 g (47.3% of theory) with a melting point of 212° C. (decomp.) and a specific rotation of $[a]_D^{25}=+111°$ (c=1, $CH_3OH$).

4.1.34 Example 34

(−)-(1R,5S,2"R)-2'-amino-2-o(2-methoxypropyl)-5,9,9-trimethyl-6,7-benzomorphan dihydrochloride a) Preparation of the starting compound The (±)-2'-nitro-5,9,9-trimethyl-6,7-benzomorphan required here and in other Examples is not known from the prior art. It can be prepared for example by nitrogenation of the (±)-5,9,9-trimethyl-6,7-benzomorphan (Example 30) analogously to a method described by E. L. May and E. M. Fry [J. Org. Chem. 22 (1957) 1366]. The resulting intermediate compound is crystallised from an ethanol-ether mixture as the hydrochloride, melting at 289° C. (decomp.).

b) Acylation 2.97 g (0.01 mol) of (±)-2'-nitro-5,9,9-trimethyl-6,7-benzomorphan hydrochloride are acylated in the presence of 3.04 g (0.03 mol) of triethylamine analogously to Example 1 with 1.35 g (0.011 mol) of (R)-2-methoxypropionic acid chloride. After working up, 3.5 g (about 100% of theory) of the intermediate product of type (3) are obtained.

c) Catalytic hydrogenation of the 2'-nitro- to the 2'-amino-group 3.5 g of the intermediate product resulting from step b) are dissolved in 70 ml of methanol and hydrogenated in the presence of 0.4 g of palladium on charcoal (Pd content: 5%) at 20° C. under a hydrogen pressure of 5 bar. The uptake of hydrogen ceases after 4 hours, after the calculated amount has been consumed. After the catalyst has been filtered off the reaction mixture is evaporated down, finally at 80° C. under a total water jet vacuum. Residue: 3.1 g (about 100% of theory).

d) Reduction with lithium aluminium hydride

The evaporation residue (3.1 g) obtained above is reduced analogously to Example 1 with 1.3 g of lithium aluminium hydride (lithium tetrahydridoalanate). The resulting mixture of the two expected diastereomeric bases (2.7 g) is separated analogously to Example 2 by column chromatography on 500 g of silica gel. The slower running substance (0.7 g, $R_f$=0.65) is crystallised as the dihydrochloride analogously to Example 2 (but with two equivalents of hydrochloric acid). The title compound is obtained in a yield of 0.95 g (50.6% of theory) and with a melting point of 260° C. (decomp.) and a specific rotation of $[a]_D^{25}=-93.4°$ (c=1, $CH_3OH$)

4.1.35 Example 35

(+)-(1S,5R,2"R)-2'-amino-2-(2-methoxypropyl)-5,9,9-trimethyl-6,7-benzomorphan dimethanesulphonate 0.9 g of the faster running substance ($R_f$=0.70) separated in Example 34 are crystallised from a mixture of methanol and diethylether analogously to Example 28 (but with 2 equivalents of methanesulphonic acid). The title compound is obtained in a yield of 0.48 g (19.4% of theory) with a melting point of 189° C. (decomp) and a specific rotation of $[\alpha]_D^{25}=+55.6°$ (c=1, $CH_3OH$).

4.1.36 Example 36

(+)-(1S,5R,2"S)-2'-amino-2-(2-methoxypropyl)-5,9,9-trimethyl-6,7-benzomorphan hydrochloride Starting from 2.97 g (0.01 mol) of (±)-2'-nitro-5,9,9-trimethyl-6,7-benzomorphan hydrochloride, 3.04 g (0.03 mol) of triethylamine and 1.35 g (0.011 mol) of (S)-2-methoxypropionic acid chloride, 3.5 g (around 100% of theory) of the acylation product are obtained which, as described therein, is catalytically hydrogenated (producing 3.2 g of hydrogenation product) and then reduced with lithium aluminium hydride (lithium tetrahydroalanate). The reduction product (2.8 g), consisting of a mixture of the expected diastereomeric bases, is dissolved in 10 ml of isopropanol with heating. Over a period of about 12 hours, as the mixture is left to stand in the refrigerator, the substance which is slower running in chromatography ($R_f$= 0.65) crystallises as a base (0.75 g =49.0% of theory) with a melting point of 142° C. Of this, 0.3 g were crystallised as the dihydrochloride analogously to Example 32. The title compound (0.37 g) is obtained with a melting point of 265° C. (decomp.) and a specific rotation of $[\alpha]_D^{25}=+92.5°$ (c=1, $CH_3OH$)

4.1.37 Example 37

(−)-(1R,5S,2"S)-2'-amino-2-(2-methoxy-propyl)-5,9,9-trimethyl-6,7-benzomorphan dihydrochloride The isopropanol mother liquor of Example 34 is evaporated down and the residue (2.0 g) is chromatographed on 300 g of silica gel analogously to Example 2. The faster running diastereomer (1.2 g, $R_f$=0.70) together with another 0.3 g of the slower running substance ($R_f$=0.65, Example 34) is crystallised as the dihydrochloride analogously to Example 32. The title compound is obtained in a yield of 1.48 g (78.8% of theory) with a melting point of 259° C. (decomp.) and a specific rotation of $[\alpha]_D^{25}=-68.4°$ (c=1, $CH_3OH$).

4.1.38 Example 38

(±)-2'-hydroxy-2-(2-methoxyisobutyl)-5,9,9-trimethyl-6,7-benzomorphan hydrobromide Starting from 1.16 g (0.005 mol) of (±)-2'-hydroxy-5,9,9-trimethyl-6,7-benzomorphan and 0.75 g (0.055 mol) of 2-methoxyisobutyric acid chloride, first the base form of the title compound (1.1 g) is obtained analogously to Example 1. This is dissolved in 5 ml of methanol and after acidification with (62%) HBr the solution is mixed with diethylether until turbidity is just setting in. When left to stand for about 12 hours in the refrigerator the title compound crystallises out, is suction filtered, washed with a mixture of ethanol and ether and dried at 80° C. Yield 1.1 g (55.2% of theory), melting point 232° C. (decomp.). A sample recrystallised from methanol-ether mixture melts at 240° C. (decomp.).

4.1.39 Example 39

(−)-(1R,5S,2"R)-2'-hydroxy-2-(2-methoxybutyl)-5,9,9-trimethyl-6,7-benzomorphan hydrochloride a) Preparation of the starting compound The (R)-2-methoxy-butyric acid chloride needed in this and other Examples may, for example, be prepared from the known (R)-2-methoxybutyric acid [N. K. Kochetkov, A. M. Likhosherstov and V. N. Kulakov, Tetrahedron 25 (1969) 2313] and thionylchloride at ambient temperature. The acid chloride remaining after the excess thionylchloride has been removed is used in the next reaction step without any further purification.

b) Reaction to obtain the title compound

Starting from 3.47 g (0.015 mol) of (±)-2'-hydroxy-5,9,9-trimethyl-6,7-benzomorphan and 2.46 g (0.018 mol) of (R)-2-methoxybutyric acid chloride the title compound is obtained analogously to Example 1 in a yield of 1.8 g (67.8% of theory) with a melting point of 246° C. (decomp.) and a specific rotation of $[\alpha]_D^{25}=-118.4°$ (c=1, CH$_3$OH).

4.1.40 Example 40

(+)-(1S,5R,2"R)-2'-hydroxy-2-(2-methoxybutyl)-5,9,9-trimethyl-6,7-benzomorphan hydrochloride The mother liquor obtained in Example 39 is evaporated down. From the residue, the title compound is obtained analogously to Example 2 in a yield of 1.3 g (48.9% of theory) with a melting point of 228° C. (decomp.) and a specific rotation of $[\alpha]_D^{25}=+79.9°$ (c=1, CH$_3$OH).

4.1.41 Example 41

(−)-(1R,5S,2"S)-2'-hydroxy-2-(2-methoxybutyl)-5,9,9-trimethyl-6,7-benzomorphan hydrochloride a) Preparation of the starting compound The (S)-2-methoxybutyric acid chloride needed in this and in other Examples may for example be prepared from the known (S)-2-methoxy-butyric acid [Tetrahedron 25 (1969) 2322] analogously to Example 39.

b) Reaction to the title compound

Starting from 3.47 g (0.015 mol) of (±)-2'-hydroxy-5,9,9-trimethyl-6,7-benzomorphan and 2.46 g (0.018 mol) of (S)-2-methoxybutyric acid chloride, the title compound is obtained analogously to Example 1 in a yield of 1.6 g (60.3% of theory) with a melting point of 246° C. (decomp.) and a specific rotation of $[\alpha]_D^{25}=+119.2°$ (c=1, CH$_3$OH)

4.1.42 Example 42

(+)-(1S,5R,2"S)-2'-hydroxy-2-(2-methoxybutyl)-5,9,9-trimethyl-6,7-benzomorphan hydrochloride The mother liquor obtained in Example 41 is evaporated down. From the residue, the title compound is obtained analogously to Example 2 in a yield of 0.6 g (22.6% of theory) with a melting point of 228° C. (decomp.) and a specific rotation of $[\alpha]_D^{25}=-71.7°$ (c=1, CH$_3$OH).

4.1.43 Example 43

(−)-(1R,5S,2"R)-2-(2-benzyloxypropyl)-2'-hydroxy-5,9,9-trimethyl-6,7-benzomorphan hydrochloride a) Preparation of the starting compound The (R)-2-benzyloxypropionic acid chloride used here and in other Examples may for example be prepared as follows: commercial isobutyl (R)-(+)-lactate is O-benzylated with benzylbromide in the presence of silver oxide. The subsequent saponification with sodium hydroxide solution yields (R)-2-benzyloxy-propionic acid with a specific rotation of $[\alpha]_D^{25}=+79.50°$ (c=1, CH$_3$OH). The corresponding acid chloride is obtained from this analogously to Example 39.

b) Reaction to the title compound

Starting from 3.47 g (0.015 mol) of (±)-2'-hydroxy-5,9,9-trimethyl-6,7-benzomorphan and 3.3 g (0.0165 mol) of (R)-2-benzyloxypropionic acid chloride, a mixture of the expected diastereomers is obtained analogously to Example 1, which are separated by crystallisation of the corresponding hydrochlorides as described in that Example. The title compound is obtained in a yield of 2.39 g (76.6% of theory) with a melting point of 250° C. (decomp.) and a specific rotation of $[\alpha]_D^{25}=-119.3°$ (c=1, CH$_3$OH).

4.1.44 Example 44

(+)-(1S,5R,2"S)-2-(2-benzyloxypropyl)-2'-hydroxy-5,9,9-trimethyl-6,7-benzomorphan hydrochloride a) Preparation of the starting compound The (S)-2-benzyloxypropionic acid chloride used here and in other Examples may for example be prepared analogously to Example 43 from (S)-2-benzyloxypropionic acid (specific rotation: $[a]^{25}=-78.5°$ (c=1, CH$_3$OH)).

b) Reaction to the title compound

Starting from 3.47 g (0.015 mol) of (±)-2'-hydroxy-5,9,9-trimethyl-6,7-benzomorphan and 3.3 g (0.0165 mol) of (S)-2-benzyloxypropionic acid chloride the title compound is obtained analogously to Example 43 in a yield of 2.56 g (82.1% of theory) with a melting point of 250° C. (decomp.) and a specific rotation of $[\alpha]_D^{25}=+119.5°$ (c=1, CH$_3$OH).

4.1.45 Example 45

(−)-(1R,5S,2"R)-2'-hydroxy-2-(2-methylthiopropyl)-5,9,9-trimethyl-6,7-benzomorphan hydrochloride a) Preparation of the starting compound The (R)-2-methylthiopropionic acid chloride required here and in other Examples may for example be prepared analogously to Example 39 from the known (R)-2-methylthio-propionic acid (L. N. Owen and M. B. Rahman J. Chem. Soc. [c] 1971, 2432].

b) Reaction to the title compound 1.62 g (0.007 mol) of (±)-2'-hydroxy-5,9,9-trimethyl-6,7-benzomorphan are reacted analogously to Example 1 with 1.07 g (7.7 mMol) of (R)-2-methylthio-propionic acid chloride. After reduction of the reaction product with lithium aluminium hydride (LiAlH$_4$) a mixture of the expected diastereomers is obtained, which are separated by crystallisation of their nitrates. The substance which crystallises from ethanol after acidification with 65% nitric acid and the addition of diethylether until turbidity sets in is left to stand in the refrigerator for about 12 hours, then suction filtered, washed with a mixture of ethanol and ether and then with ether and dried at 80° C. The nitrite (0.67 g) is recrystallised from boiling ethanol (0.52 g), then converted into the free base and finally crystallised as the hydrochloride analogously to Example 2. The title compound is obtained in a yield of 0.43 g (34.4% of theory) with a melting point of 265° C. (decomp) and a specific rotation of $[\alpha]_D^{25}=+135.1°$ (c=0.5 CH$_3$OH).

4.1.46 Example 46

(+)-(1S,5R,2"R)-2'-hydroxy-2-(2-methylthiopropyl)-5,9,9-trimethyl-6,7-benzomorphan hydrochloride The mother liquor of the first nitrate crystallisation obtained according to Example 45 is evaporated down and the nitrate residue is converted into the free base. This (1 g) is filtered over 20 g of aluminium oxide as in Example 55 and then crystallised as the hydrochloride (ethanol/ether).

This hydrochloride (0.29 g) is recrystallised from a mixture of 2 ml of methanol and diethylether. The title compound is obtained in a yield of 0.21 g (16.8% of theory) with a melting point of 238° C. (decomp.) and a specific rotation of $[\alpha]_D^{25}=+73.0°$ (c=0.5, $CH_3OH$).

4.1.47 Example 47

(−)-(1R,5S,2"S)-2'-hydroxy-2-(2-methylthiopropyl-5,9,9-trimethyl-6,7-benzomorphan hydrochloride
a) Preparation of the starting compound The (S)-2-methylthiopropionic acid chloride needed here and in other Examples may be prepared for example from the known (S)-2-methylthiopropionic acid [J. Chem. Soc. 1971, 2437] analogously to Example 39.

b) Reaction to the title compound

Starting from 1.62 g (0.007 mol) of (±)-2'-hydroxy-5,9,9-trimethyl-6,7-benzomorphan, the title compound is obtained analogously to Example 45 in a yield of 0.42 g (33.6% of theory) with a melting point of 265° C. (decomp.) and a specific rotation of $[\alpha]_D^{25}=+135.1°$ (c=0.5, $CH_3OH$)

4.1.48 Example 48

(−)-(1R,5S,2"S)-2'-hydroxy-2-(2-methylthiopropyl-5,9,9-trimethyl-6,7-benzomorphan hydrochloride Starting from the nitrate mother liquor in Example 47, the title compound is obtained analogously to Example 46 in a yield of 0.34 g (27.2% of theory) with a melting point of 238° C. (decomp.) and a specific rotation of $[\alpha]_D^{25}=-73.9°$ (c=0.5, $CH_3OH$)

4.1.49 Example 49

(+)-(1S,5R,2"S)-2-(2-allyloxypropyl)-2'-hydroxy-5,9,9-trimethyl-6,7-benzomorphan hydrochloride
a) Preparation of the starting compound The (S)-(−)-2-allyloxy-propionic acid chloride used here may be prepared as follows, for example: commercial ethyl (S)-(−)-lactate is o-allylated with allylbromide in the presence of silver oxide. Subsequent saponification with sodium hydroxide solution yields (S)-2-allyloxy-propionic acid with a boiling point of 110° to 112° C. at a pressure of 15 mbar and a specific rotation of $[\alpha]_D^{25}78.4°$ (c=1, $CH_3OH$) The corresponding acid chloride is obtained therefrom analogously to Example 39.

b) Reaction to the title compound

Starting from 3.47 g (0.015 mol) of (±)-2'-hydroxy-5,9,9-trimethyl- 6,7-benzomorphan and 3.3 g (0.0165 mol) of (S)-2-allyloxy-propionic acid chloride, a mixture of the two expected diastereomers is obtained analogously to Example 1, which is separated as described therein by crystallisation of the corresponding hydrochlorides. The title compound is obtained in a yield of 1.4 g (51.0% of theory) with a melting point of 245° C. (decomp.) and a specific rotation of $[\alpha]_D^{25}=+120°$ (c=1, $CH_3OH$).

4.1.50 Example 50

(−)-(1S,5R,2"S)-2-(2-allyloxypropyl)-2'-hydroxy-5,9,9-trimethyl-6,7-benzomorphan hydrochloride The mother liquors obtained in Example 49 are evaporated down. From the residue, the title compound is obtained analogously to Example 2 in a yield of 0.62 g (22.6% of theory) with a melting point of 213° C. and a specific rotation of $[\alpha]_D^{25}=-38.6°$ (c=1, $CH_3OH$).

4.1.51 Example 51

(−)-(1R,5S,2"R)-2'-hydroxy-2-(2-phenoxy-propyl)-5,9,9-trimethyl-6,7-benzomorphan hydrochloride 2.31 g (0.010 mol) of (+)-2'-hydroxy-5,9,9-trimethyl-6,7-benzomorphan and 2.03 g (0.011 mol) of (R)-2-phenoxypropionic acid chloride (prepared—analogously to Example 39—from the known acid [CA 72, 12917d]) are reacted analogously to Example 1. A mixture of the two expected diastereomers is obtained which, as described therein, is separated by crystallisation of the corresponding hydrochlorides. In this way, the title compound is obtained in a yield of 1.6 g (79.6% of theory) with a melting point of 279° C. (decomp.) and a specific rotation of $[\alpha]_D^{25}=-142.9°$ (c=1, $CH_3OH$).

4.1.52 Example 52

(+)-(1S,5R,2"S)-2'-hydroxy-2-(2-phenoxypropyl)-5,9,9-trimethyl-6,7-benzomorphan hydrochloride By proceeding as in Example 1 with (S)-2-phenoxypropionic acid chloride the title compound is obtained in a yield of 1.6 g with a specific rotation of $[\alpha]_D^{25}=+143.3°$ C. (c=$CH_3OH$)

4.1.53 Example 53

(−)-(1R,5S,2"R)-3'-hydroxy-2-(2-methoxy-propyl)-5,9,9,2'-tetramethyl-6,7-benzomorphan hydrochloride
a) Starting compound The (±)-3'-hydroxy-5,9,9,2'-tetramethyl-6,7-benzomorphan required here and in other Examples is not known from the prior art. It may be prepared, for example, using the method of synthesis given for the known 2'-hydroxy derivative [DOS 20 27 077; CA 74 (1971), 125482x] using 3-methoxy-4-methylbenzyllithium instead of p-methoxybenzyllithium. The 3'-hydroxy-5,9,9,2'-tetramethyl-6,7-benzomorphan which is predominantly obtained on cyclisation to the benzomorphan system is purified by flash column chromatography (cf. Example 16).

b) Reaction to the title compound

Starting from 2.44 g (0.010 mol) of (±)-3'-hydroxy-5,9,9,2'-tetramethyl-6,7-benzomorphan and 1.6 g (0.013 mol) of (R)-2-methoxypropionic acid chloride a mixture of the expected diastereomeric bases is obtained analogously to Example 1 which are separated by column chromatography on 100 times the quantity of silica gel, analogously to Example 2. The slower running substance ($R_f$=0.25) is crystallised out as the hydrochloride. The title compound is obtained in a yield of 1.06 g (59.9%) with a melting point of 181°–182° C. and a specific rotation of $[\alpha]_D^{25}=-89.5°$ (c=1, $CH_3OH$).

4.1.54 Example 54

(+)-(1S,5R,2"R)-3'-hydroxy-2-(2-methoxy-propyl)-5,9,9,2'-tetramethyl-6,7-benzomorphan hydrochloride The faster running substance ($R_f$=0.34) separated off in Example 53 is precipitated as the hydrochloride analogously to Example 2. The title compound is obtained in a yield of 1.24 g (70.1%) as an amorphous powder with a specific rotation of $[\alpha]_D^{25}=+55.9°$ (c=1, $CH_3OH$).

4.1.55 Example 55

(+)-(1S,5R,2"S)-3'-hydroxy-2-(2-methoxy-propyl)-5,9,9,2'-tetramethyl-6,7-benzomorphan hydrochloride Starting from 2.44 g (0.010 mol) of (±)-3'-hydroxy-5,9,9,2'-tetramethyl-6,7-benzomorphan (see Example 53) and 1.6 g (0.013 mol) of (S)-2-methoxy-propionic acid chloride a mixture of the expected diastereomeric bases is obtained analogously to Example 1 which are separated by column chromatography on 100 times the quantity of silica gel analogously to Example 2. The slower running substance ($R_f$=0.25) is crystallised out in the form of the hydrochloride. The title compound is obtained in a yield of 1.48 g (83.6%) with a melting point of 186°–188° C. and a specific rotation of $[a]_D^{25}$=+88.2° (c=1, $CH_3OH$)

4.1.56 Example 56

(−)-(1R,5S,2"S)-3'-hydroxy-2-(2-methoxypropyl)-5, 9,9,2'-tetramethyl-6,7-benzomorphan hydrochloride The faster running substance ($R_f$=0.34) separated off in Example 55 is precipitated as the hydrochloride analogously to Example 2. The title compound is obtained in a yield of 1.40 g (79.1%) as an amorphous powder with a specific rotation of $[\alpha]_D^{25}$=56.8° (c=1, $CH_3OH$).

4.1.57 Example 57

()-(1R,5S,2"R)-2'-hydroxy-2-(2-methoxypropyl)-5,9, 9,3'-tetramethyl-6,7-benzomorphan methanesulphonate a) Starting compound The (±)-2'-hydroxy-5,9,9,3'-tetramethyl-6,7-benzomorphan required here and in other Examples is not known from the prior art. It may, for example, be prepared by the method of synthesis given for the known 2'-hydroxy derivative [DOS 20 27 077; CA 74 (1971), 125482x], using 4-methoxy-3-methylbenzyllithium instead of p-methoxybenzyllithium. The 2'-hydroxy-5,9,9,3'-tetramethyl-6,7-benzomorphan which is predominantly obtained on cyclisation to form the benzomorphan system is purified by flash column chromatography (cf. Example 16).

b) Reaction to obtain the title compound

Starting from 2.44 g (0.010 mol) of (±)-2'-hydroxy-5,9, 9,3'-tetramethyl-6,7-benzomorphan and 1.6 g (0.013 mol) of (R)-2-methoxypropionic acid chloride a mixture of the expected diastereomeric bases is obtained analogously to Example 1, which is separated by column chromatography on 100 times the quantity of silica gel analogously to Example 2. The slower running substance ($R_f$=0.26) is crystallised out as the methanesulphonate. The title compound is obtained in a yield of 1.64 g (79.3%) with a melting point of 266°–268° C. and a specific rotation of $[\alpha]_D^{25}$=−95.4° (c=1, $CH_3OH$)

4.1.58 Example 58

(+)-(1S,5R,2"R)-2'-hydroxy-2-(2-methoxy-propyl)-5,9,9,3'-tetramethyl-6,7-benzomorphan hydrochloride The faster running substance ($R_f$=0.29) separated off in Example 57 is precipitated as the hydrochloride analogously to Example 2. The title compound is obtained in a yield of 1.60 g (90.4%) as an amorphous powder with a specific rotation of $[\alpha]_D^{25}$=+73.4° (c=1, $CH_3OH$).

4.1.59 Example 59

(+)-(1S,5R,2"S)-2'-hydroxy-2-(2-methoxy-propyl)-5, 9,9,3'-tetramethyl-6,7-benzomorphan methanesulphonate Starting from 2.44 g (0.010 mol) of (±)-2'-hydroxy-5,9, 9,3'-tetramethyl-6,7-benzomorphan (see Example 57) and 1.6 g (0.013 mol) of (S)-2-methoxy-propionic acid chloride, a mixture of the expected diastereomeric bases is obtained analogously to Example 1, which is separated by column chromatography on 100 times the amount of silica gel analogously to Example 2. The slower running substance ($R_f$=0.26) is crystallised out as the methanesulphonate. The title compound is obtained in a yield of 1.56 g (88.1%) with a melting point of 265°–267° C. and a specific rotation of $[\alpha]_D^{25}$=+96.9° (c=1, $CH_3OH$).

4.1.60 Example 60

(−)-(1R,5S,2"S)-2'-hydroxy-2-(2-methoxy-propyl)-5, 9,9,3'-tetramethyl-6,7-benzomorphan hydrochloride The faster running substance ($R_f$=0.29) separated in Example 59 is precipitated as the hydrochloride analogously to Example 2. The title compound is obtained in a yield of 1.36 g (76.8%) as an amorphous powder with a specific rotation of $[\alpha]_D^{25}$=−74.9° (c=1, $CH_3OH$).

4.1.61 Example 61

(−)-(1R,5S,2"R)-2',3'-dihydroxy-2-(2-methoxypropyl)-5,9,9-trimethyl-6,7-benzomorphan hydrochloride a) Starting compound The (±)-2',3'-dihydroxy-5,9,9-trimethyl-6,7-benzomorphan required here and in other Examples is not known from the prior art. It may, for example, be prepared by the method of synthesis given for the known 2'-hydroxy derivative [DOS 20 27 077; CA 74 (1971), 125482x], using 3,4-dimethoxybenzyllithium instead of p-methoxybenzyllithium. The 2',3'-dihydroxy-5,9,9-trimethyl-6,7-benzomorphan predominantly obtained on cyclisation to form the benzomorphan system is purified by flash column chromatography (cf. Example 16).

b) Reaction to form the title compound

Starting from 8.51 g (0.03 mol) of (±)-2',3'-dihydroxy-5, 9,9-trimethyl-6,7-benzomorphan hydrochloride and 4.1 g (0.033 mol) of (R)-2-methoxy-propionic acid chloride, a mixture of the expected diastereomeric bases is obtained analogously to Example 1, which is separated analogously to Example 2 by column chromatography on 100 times the amount of silica gel. The slower running substance ($R_f$=0.21) is crystallised out as the hydrochloride.

The title compound is obtained in a yield of 2.54 g (47.6%) with a melting point of 167° (decomp.) and a specific rotation of $[\alpha]_D^{25}$=98.6° (c=0 5; $CH_3OH$)

4.1.62 Example 62

(+)-(1S,5R,2"R)-2',3'-dihydroxy-2-(2-methoxypropyl)-5,9,9-trimethyl-6,7-benzomorphan hydrochloride The faster running substance ($R_f$=0.29) separated off in Example 61 is precipitated as the hydrochloride analogously to Example 2. The title compound is obtained in a yield of 2.28 g (42.7%) with a melting point of 251° C. (decomp.) and with a specific rotation of $[\alpha]_D^{25}$=+64.3° (c=0.5; $CH_3OH$).

4.2 Compounds (1) according to process 3.2

4.2.1 Example 63

(±)-2'-hydroxy-2-(2-methoxyethyl)-5,9,9-trimethyl-6,7-benzomorphan hydrobromide 0.6 g (0.003 mol) of (±)-2'-hydroxy-5,9,9-trimethyl-6,7-benzomorphan, 0.72 g (0.0075 mol) of 2-methoxyethylchloride, 0.11 g (0.0075 mol) of sodium iodide and 0.95 g (0.0113 mol) of sodium hydrogen carbonate are stirred in 10 ml of absolute dimethylformamide at 95° C. for 23 hours. The reaction mixture is evaporated down in a rotary evaporator, finally at 95° C. under a total water jet vacuum. The residue is shaken with 25 ml of water and 25 ml of dichloromethane and the aqueous phase separated off is extracted once more with 10 ml of dichloromethane. The combined extracts are washed with water, dried with sodium sulphate and, after filtration of the drying agent, as described above, evaporated down in vacuo. The evaporation residue consisting of the free base of the title compound is crystallised as the hydrobromide analogously to Example 38. The title compound is obtained in a yield of 0.48 g (43.5% of theory) with a melting point of 247° C. (decomp.).

4.2.2 Example 64

(−)-(1R,5S,2"R)-2'-hydroxy-2-(2-methoxy-propyl)-5,9,9-trimethyl-6,7-benzomorphan hydrochloride a) Preparation of the alkylating agent By reduction of the (+)-(R)-2-methoxy-propionic acid known from the prior art with lithium aluminium hydride (LiAlH$_4$) the (−)-(R)-2-methoxy-propanol is obtained with a boiling point of 70° C. under a pressure of 76 mbar and a specific rotation of $[\alpha]_D^{25}$=−15.8° (c=100). The corresponding (+)-(S)-2-methoxy-propanol with a boiling point of 70° C. under a pressure of 76 mbar and a rotation of $[\alpha]_D^{25}$=+16.5° (c=100) is obtained analogously from the equally well known (−)-(S)-2-methoxy-propionic acid.

By reacting (−)-(R)-2-methoxypropanol with p-toluenesulphonic acid chloride in pyridine analogously to R. S. Tipson [J. Org. Chem. 9 (1944) 235] the (+)-(R)-2-methoxypropyl-p-toluenesulphonate is obtained in the form of a yellowish oil with a specific rotation of $[\alpha]_D^{25}$=+3.7° (c=100) and analogously, from (+)-(S)-2-methoxy-propanol, the corresponding (−)-(S)-2-methoxypropyl-p-toluenesulphonate is obtained with a rotation of $[\alpha]_D^{25}$=−3.7° (c=100).

b) Reaction to form the title compound 1.16 g (5 mMol) of (±)-2'-hydroxy-5,9,9-trimethyl-6,7-benzomorphan (Example 1) are heated to reflux temperature with 1.83 g (7.5 mMol) of (R)-2-methoxy-propyl-p-toluenesulphonate, 1.26 g (0.015 mol) of sodium hydrogen carbonate and 1.12 g (7.5 mMol) of sodium iodide in a mixture of 15 ml of absolute dimethylformamide and 25 ml of absolute tetrahydrofuran for 60 hours with stirring. Then the mixture is worked up analogously to Example 63. A mixture of the two expected diastereomeric bases (2 g) is obtained which can also be prepared by other methods according to Example 1. The mixture is separated by crystallisation of the hydrochlorides as described in Example 1 and the title compound is obtained in a yield of 0.55 g (64.7% of theory) with a melting point of 264° C. (decomp.) and a specific rotation of $[\alpha]_D^{25}$=−118.2° (c=1, CH$_3$OH). The (+)-(1S,5R,2"R)-diastereomer can be obtained from the mother liquor analogously to Example 2.

4.2.3 Example 65

(−)-(1R,5S,2"R)-2-(2-methoxypropyl)-2'-nitro-5,9,9-trimethyl-6,7-benzomorphan hydrochloride 2.97 g (0.010 mol) of (±)-2'-nitro-5,9,9-trimethyl-6,7-benzomorphan hydrochloride (Example 34) are reacted analogously to Example 64 with 2.68 g (0.011 mol) of (R)-2-methoxypropyl-p-toluenesulphonate, 1.65 g (0.011 mol) of sodium iodide and 2.1 g (0.025 mol) of sodium hydrogen carbonate. The reaction product which is isolated as described consists initially of a mixture of the two expected diastereomeric bases (3.2 g). In order to separate off any by-products this mixture is dissolved in 64 ml of dichloromethane and the solution is filtered through a column containing 64 g of aluminium oxide (activity stage III—neutral—according to Brockmann). After eluting with a further 128 ml of dichloromethane, the combined eluates are evaporated down in a rotary evaporator, finally at 80° C. under a total water jet vacuum. The residue (2.4 g) is dissolved in 10 ml of methanol and after acidification with 2.5N ethanolic hydrochloric acid the solution is mixed with diethylether until it is just beginning to be cloudy. The title compound is crystallised and after standing for 3 days at ambient temperature it is suction filtered, washed with ethanol/ether mixture (1:1), then with ether and dried at 80° C. The title compound is obtained in a yield of 0.84 g (45.5% of theory) with a melting point of 226° C. (decomp.) and a specific rotation of $[\alpha]_D^{25}$=−120° (c=1, CH$_3$OH). The stereoisomeric (+)-(1S,5R,2"R) compound may be obtained from the mother liquor if desired.

4.2.4 Example 66

(+)-(1S,5R,2"S)-2-(2-methoxypropyl)-2'-nitro-5,9,9-trimethyl-6,7-benzomorphan hydrochloride Starting from 2.97 g (0.010 mol) of (±)-2'-nitro-5,9,9-trimethyl-6,7-benzomorphan hydrochloride and 2.68.g (0.011 mol) of (S)-2-methoxypropyl-p-toluenesulphonate, the title compound is obtained analogously to Example 65 in a yield of 0.96 g (52.0% of theory) with a melting point of 226° C. (decomp.) and a specific rotation of $[\alpha]_D^{25}$=+121° (c=CH$_3$OH) The stereoisomeric (−)-(1R,5S 2"S) form can be obtained from the mother liquor analogously to Example 2.

4.2.5 Example 67

(−)-(1R,5S,2"R)-2-(2-methoxypropyl)-3'-nitro-5,9,9-trimethyl-6,7-benzomorphan a) Preparation of the starting compound (±)-3'-nitro-5,9,9-trimethyl-6,7-benzomorphan required here and in other Examples is formed in addition to the (±)-2'-nitro-isomer when 5,9,9-trimethyl-6,7-benzomorphan (Example 34) is nitrogenated in a ratio of about 1:3. It is obtained from the mother liquor of the 2'-nitro-isomer, which is crystallised as the hydrochloride, via the base which is prepared initially. This is crystallised as the oxalate (melting point 158° C. (decomp.)) from ten times the amount of methanol. The oxalate is converted back into the base (not crystallised) which is used for the reaction described below. A sample of the base, crystallised as the methanesulphonate, melts at 242° C. (decomp.).

b) Reaction to form the title compound 5.2 g (0.02 mol) of (±)-3'-nitro-5,9,9-trimethyl-6,7-benzomorphan are reacted analogously to Example 65 with 5.36 g (0.022 mol) of (R)-2-methoxypropyl-p-toluenesulphonate. The reaction product obtained is a mixture of the two expected stereoisomeric bases (8 g) which is purified by filtering over aluminium oxide as described in Example 65 (4.7 g of purified base mixture). In thin layer chromatography (silica gel 60, toluene/ethyl acetate 85:15, developed 3 times) the diastereomers have $R_f$-values of 0.81 and 0.85. Separation of 1 g of diastereomer mixture on 300 g of silica gel by column chromatography yields the title compound (100 mg) with an $R_f$-value of 0.81 as a brownish, very viscous oil which does not crystallise.

4.2.6 Example 68

(+)-(1S,5R,2"R)-2-(2-methoxypropyl)-3'-nitro-5,9,9-trimethyl-6,7-benzomorphan

During the column chromatography of the diastereomer mixture described in Example 67, in addition to the (–)-(1R,5S,2"R)-form isolated there ($R_f$=0.81), 100 mg of the (+)-(1S,5R,2"S)-form ($R_f$=0.85) are also obtained as a brownish, highly viscous oil which does not crystallise.

4.2.7 Example 69

(–)-(1R,5S,2"R)-2'-chloro-2-(2-methoxy-propyl)-5,9,9-trimethyl-6,7-benzomorphan hydrochloride a) Preparation of the starting compound (±)-2'-chloro-5,9,9-trimethyl-6,7-benzomorphan used here and in other Examples may be prepared from the 2'-nitro analogue (Example 34), for example, by hydrogenating the latter to form the 2'-amino compound (dihydrochloride: melting point 283° C., (decomp.)) and converting this by Sandmeyer reaction into the desired 2'-chloro-compound (hydrobromide: melting point >310° C. (decomp.).

b) Reaction to form the title compound 3.3 g (0.010 mol) of (±)-2'-chloro-5,9,9-trimethyl-6,7-benzomorphan hydrobromide and 2.68 g (0.011 mol) of (R)-2-methoxypropyl-p-toluenesulphonate are reacted analogously to Example 65 to form a mixture of the two expected diastereomeric bases and purified by filtration over aluminium oxide as described therein. The purified diastereomer mixture is separated analogously to Example 1 by crystallisation of the hydrochlorides. The title compound is obtained in a yield of 0.27 g (15.1% of theory) with a melting point of 287° (decomp.) and a rotation of $[\alpha]_D^{25}$=–102.6° (c=1, CH$_3$OH)

4.2.8 Example 70

(+)-(1S,5R,2"R)-2'-chloro-2-(2-methoxypropyl)-5,9,9-trimethyl-6,7-benzomorphan hydrochloride The mother liquor of Example 69 is evaporated down and the residue is dissolved with a barely sufficient quantity of boiling methanol. After the addition of diethylether until the mixture is beginning to be cloudy and after simultaneous crystallisation the title compound is obtained. After standing for about 12 hours at ambient temperature this title compound is suction filtered, washed with ethanol/ether 1:1 and then with ether and dried at 80° C. Yield 0.56 g (31.3% of theory), melting point: 289° C., specific rotation: $[\alpha]_D^{25}$=+67.9°.

4.2.9 Example 71

(+)-(1S,5R,2"S)-2'-chloro-2-(2-methoxypropyl)-5,9,9-trimethyl-6,7-benzomorphan hydrochloride Starting from 3.3 g (0.010 mol) of (±)-2'-chloro-5,9,9-trimethyl-6,7-benzomorphan and 2.68 g (0.011 mol) of (S)-2-methoxypropyl-p-toluenesulphonate the title compound is obtained analogously to Example 69 in a yield of 0.41 g (22.9% of theory) with a melting point of 288° C. (decomp) and a specific rotation of $[\alpha]_D^{25}$=+101.7° (c=1, CH$_3$OH).

4.2.10 Example 72

(–)-(1R,5S,2"S)-2'-chloro-2-(2-methoxypropyl)-5,9,9-trimethyl-6,7-benzomorphan hydrochloride From the mother liquors of Example 71 the title compound is obtained analogously to Example 70 in a yield of 0.75 g (41.9% of theory) with a melting point of 288° C. and a specific rotation of $[\alpha]_D^{25}$=–68.6° (c=1, CH$_3$OH)

4.3 Compounds (1) according to process 3.3

4.3.1 Example 73

(–)-(1R,5S,2"S)-2'-methoxy-2-(2-methoxy-propyl)-5,9,9-trimethyl-6,7-benzomorphan methanesulphonate 0.68 g (2 mMol) of (–)-(1R,5S,2"S)-2'-hydroxy-2-(2-methoxypropyl)-5,9,9-trimethyl-6,7-benzomorphan hydrochloride (Example 4) are placed in 20 ml of absolute dimethylformamide and, whilst cooling with ice and stirring, 0.13 g of 77% sodium hydride suspension in paraffin (4.2 mMol) are added thereto. After 30 minutes stirring, 0.31 g. (2.2 mMol) of methyliodide, dissolved in 5 ml of dimethylformamide, are added dropwise within 5 minutes. The mixture is then stirred for a further 3 hours at ambient temperature and evaporated down in the rotary evaporator, finally at 95° C. under a total water jet vacuum. The residue is shaken with 25 ml of dichloromethane and 25 ml of water. The aqueous phase separated off is extracted once more with 15 ml of dichloromethane. After washing with 15 ml of water the combined extracts are evaporated down and the residue is crystallised as the methanesulphonate analogously to Example 28. The title compound is obtained in a yield of 0.38 g (46.0%) with a melting point of 150°–152° C. (decomp.) and a specific rotation of $[\alpha]_D^{25}$=–68.7° (c=1, CH$_3$OH).

4.3.2 Example 74

(+)-(1S,5R,2"R)-2'-methoxy-2-(2-methoxy-propyl)-5,9,9-trimethyl-6,7-benzomorphan methanesulphonate Starting from 0.68 g (2 mMol) of (+)-(1S,5R,2"R)-2'-hydroxy-2-(2-methoxypropyl)-5,9,9-trimethyl-6,7-benzomorphan hydrochloride (Example 2), the title compound is obtained analogously to Example 73 in a yield of 0.38 g (46.0% of theory) with a melting point of 150°–152° C. (decomp.) and a specific rotation of $[\alpha]_D^{25}$=+67.2° (c=1, CH$_3$OH).

4.3.3 Example 75

(–)-(1R,5S,2"R)-2'-ethoxy-2-(2-methoxypropyl)-5,9,9-trimethyl-6,7-benzomorphan methanesulphonate Starting from 0.34 g (1 mMol) of (–)-(1R,5S,2"R)-2'-hydroxy-2-(2-methoxypropyl)-5,9,9-trimethyl-6,7-benzomorphan hydrochloride (Example 1) and 0.17 g (0.0011 mol) of ethyliodide the title compound is obtained analogously to Example 73 in a yield of 0.30 g (70.2% of theory) with a melting point of 146°–148° C. (decomp.) and a specific rotation of $[\alpha]_D^{25}$=–93.4° (c=1, CH$_3$OH).

4.3.4 Example 76

(–)-(1R,5S,2"R)-2'-acetoxy-2-(2-methoxy-propyl)-5,9,9-trimethyl-6,7-benzomorphan methanesulphonate 0.68 g (2 mMol) of (–)-(1R,5S,2"R)-2'-hydroxy-2-(2-methoxypropyl)-5,9,9-trimethyl-6,7-benzomorphan hydrochloride (Example 1) are dissolved in 15 ml of absolute dichloromethane. After the addition of 0.51 g (5 mMol) of triethylamine the solution is mixed with 0.19 g (2.4 mMol) of acetylchloride dissolved in 5 ml of dichloromethane, with stirring, at ambient temperature, over a period of 10 minutes. Then the resulting mixture is stirred for a further 2 hours at ambient temperature. It is then washed three times with 10 ml of ice water, dried with sodium sulphate and, after the drying agent has been filtered off, the residue is evaporated down (rotary evaporator, finally at a temperature of 80° C. under a total water jet vacuum).

The residue, which consists of the free base of the title compound (0.6 g, 1.74 mMol), is dissolved in 3 ml of ethanol and acidified to just pH 4 by the addition of methanesulphonic acid (0.16 g, (1.74 mMol) in 3 ml of ethanol). After the addition of diethylether until the mixture is just turning cloudy the title compound crystallises and, after being left to stand for about 12 hours in the refrigerator, it is suction filtered, washed with ethanol/ether 1:2 and dried at 80° C. Yield 0.7 g (79.3% of theory), melting point: 183°–184° C. (decomp), $[\alpha]_D^{25}=-83.9°$ (c=1, $CH_3OH$).

4.3.5 Example 77

(+)-(1S,5R,2"S)-2'-acetoxy-2-(2-methoxy-propyl)-5,9,9-trimethyl-6,7-benzomorphan methanesulphonate Starting from 0.68 g (0.002 mol) of (+)-(1S,5R,2"S)-2'-hydroxy-2-(2-methoxypropyl)-5,9,9-trimethyl-6,7-benzomorphan hydrochloride (Example 3) the title compound is obtained analogously to Example 76 in a yield of 0.6 g (68.0% of theory) with a melting point of 183°–184° C. (decomp.) and a specific rotation of $[\alpha]_D^{25}=+82.8°$ (c=1, $CH_3OH$).

4.3.6 Example 78

(–)-(1R,5S,2"S)-2'-acetoxy-2=(2-methoxy-propyl)-5,9,9-trimethyl-6,7-benzomorphan methanesulphonate Starting from 0.68 g (0.002 mol) of (–)-(1R,5S,2"S)-2'-hydroxy-2-(2-methoxypropyl)-5,9,9-trimethyl-6,7-benzomorphan hydrochloride (Example 4) the title compound is obtained analogously to Example 76 in a yield of 0.58 g (65.7% of theory) with a melting point of 183° C. (decomp.) and a specific rotation of $[\alpha]_D^{25}=-57.1°$ (c=1, $CH_3OH$).

4.3.7 Example 79

(+)-(1S,5R,2"R)-2'-acetoxy-2-(2-methoxy-propyl)-5,9,9-trimethyl-6,7-benzomorphan methanesulphonate Starting from 0.68 g (2 mMol) of (+)-(1S,5R,2"R)-2'-hydroxy-2-(2-methoxypropyl)-5,9,9-trimethyl-6,7-benzomorphan hydrochloride (Example 2) the title compound is obtained analogously to Example 76 in a yield of 0.67 g (75.9% of theory) with a melting point of 183° C. and a specific rotation $[\alpha]_D^{25}=+58.2°$ (c=1, $CH_3OH$).

4.3.8 Example 80

(–)-(1R,5S,2"R)-2-(2-methoxypropyl)-2'-propionoxy-5,9,9-trimethyl-6,7-benzomorphan methanesulphonate Starting from 0.34 g (1 mMol) of (–)-(1R,5S,2"R)-2'-hydroxy-2-(2-methoxypropyl)-5,9,9-trimethyl-6,7-benzomorphan hydrochloride (Example 1) and 0.15 g (1.1 mMol) of propionic acid anhydride, the title compound is obtained analogously to Example 76 in a yield of 0.21 g (46.1% of theory) with a melting point of 145° C. (decomp.) and a specific rotation of $[\alpha]_D^{25}=-78.3°$ (c=1, $CH_3OH$).

4.3.9 Example 81

(–)-(1R,5S,2"R)-2-(2-methoxypropyl)-5,9,9-trimethyl-6,7-benzomorphan hydrochloride a) (–)-(1R,5S,2"R)-2-(2-methoxypropyl)-2'-(1-phenyl-5-tetrazolyloxy)-5,9,9-trimethyl-6,7-benzomorphan hydrochloride 1.36 g (4 mMol) of (–)-(1R,5S,2"R)-2'-hydroxy-2-(2-methoxypropyl)-5,9,9-trimethyl-6,7-benzomorphan hydrochloride (Example 1) are refluxed with 0.79 g (4.4 mMol) of 5-chloro-1-phenyltetrazole and 1.36 g (0.01 mol) of dry, finely powdered potassium carbonate in 78 ml of absolute acetone for 6 days with stirring. Then the solution is evaporated down and the residue is mixed with 50 ml of water. It is extracted twice with 25 ml of dichloromethane and the combined extracts are washed with 15 ml of water. After drying with sodium sulphate and filtering off the drying agent the reaction mixture is evaporated in a rotary evaporator, finally at 80° C. under a total water jet vacuum. The residue is dissolved with 5 ml of ethanol and, after acidifying with ethanolic hydrochloric acid, mixed with diethylether until just turning cloudy. The intermediate product crystallises out and, after standing for about 12 hours in the refrigerator, is suction filtered, washed with an ethanol/ether mixture (1:1), then with ether and dried at 80° C. Yield 1.67 g (86.3% of theory), melting point 241° C. (decomp.).

b) Hydrogenation of the intermediate product to obtain the title compound

The intermediate product (1.67 g, 3.5 mMol) is hydrogenated in the presence of 0.7 g of 10% palladium/charcoal in 70 ml of glacial acetic acid under a hydrogen pressure of 5 bar and at ambient temperature until fully reacted (6–10 hours). Then the catalyst is removed by suction filtering, the filtrate is evaporated down and the residue, after being mixed with 50 ml of water and excess ammonia, is extracted with dichloromethane (twice with 25 ml). The combined extracts are washed with water, dried with sodium sulphate and evaporated down after the drying agent has been filtered off in a rotary evaporator, finally at 80° C. under a full water jet vacuum. The residue is crystallised as the hydrochloride analogously to Example 2. The title compound is obtained in a total yield of 0.5 g (38.5% of theory) with a melting point of 225° C. (decomp.) and a specific rotation of $[\alpha]_D^{25}=-101.5°$ (c=1, $CH_3OH$).

4.3.10 Example 82

(+)-(1S,5R,2"S)-2-(2-methoxypropyl)-5,9,9-trimethyl-6,7-benzomorphan hydrochloride Starting from 1.36 g (0.004 mol) of (+)-(1S,5R,2"S)-2'-hydroxy- 2-(2-methoxypropyl)-5,9,9-trimethyl-6,7-benzomorphan hydrochloride (Example 3) the title compound is obtained, analogously to Example 1 by means of the corresponding intermediate product (1.65 g, 85.1% of theory, melting point 241° (decomp.)), in a total yield of 0.64 g (49.4% of theory) with a melting point of 225° C. (decomp.) and a specific rotation of $[\alpha]_D^{25}=+106.9°$ (c=1, $CH_3OH$).

4.3.11 Example 83

(–)-(1R,5S,2"S)-2-(2-methoxypropyl)-5,9,9-trimethyl-6,7-benzomorphan oxalate

Starting from 1.36 g (4 mMol) of (–)-(1R,5S,2"S)-2'-hydroxy-2-(2-methoxypropyl)-5,9,9-trimethyl-6,7-benzomorphan hydrochloride (Example 4) the title compound is obtained in the form of the free base (0.7 g) via the corresponding intermediate product (1.73 g, 89.4% of theory, melting point 218.5° C. (decomp.). This base is dissolved with 2 ml of isopropanol and mixed with the corresponding molecular quantity of oxalic acid (0.22 g). The title compound is crystallised while 50 ml of diethylether are gradually added with stirring. After being kept for about 12 hours in the refrigerator the mixture is suction filtered, washed with isopropanol/ether, then with ether and dried at 80° C. The title compound is obtained in a yield of 0.8 g (53.0% of theory) with a melting point of 135° C. (decomp.) and a specific rotation of $[\alpha]_D^{25}=-60.0°$ (c=1, $CH_3OH$)

4.3.12 Example 84

(+)-(1S,5R,2"R)-2-(2-methoxypropyl)-5,9,9-trimethyl-6,7-benzomorphan oxalate

Starting from 1.36g (4 mMol) of (+)-(1S,5R,2"R)-2'-hydroxy-2-(2-methoxypropyl)-5,9,9-trimethyl-6,7-benzomorphan hydrochloride (Example 2) the base of the title compound is obtained analogously to Example 1 via the corresponding intermediate product (1.65 g, 85.1% of theory, melting point 217° C. (decomp.)), and is crystallised out as the oxalate analogously to Example 83. Total yield 0.6 g (39.7% of theory), melting point: 135° C. (decomp.), specific rotation: $[\alpha]_D^{25}=+60.2°$ (c=1, $CH_3OH$)

4.3.13 Example 85

(−)-(1R,5S,2"R)-2'-acetamido-2-(2-methoxypropyl)-5,9,9-trimethyl-6,7-benzomorphan hydrochloride 0.70 g (1.87 mmol) of (−)-(1R,5S,2"R)-2'-amino-2-(2-methoxypropyl)-5,9,9-trimethyl-6,7-benzomorphan dihydrochloride (Example 34) are dissolved in 20 ml of absolute dichloromethane, mixed with 0.76 g (7.4 mMol) of triethylamine and then, with stirring, at ambient temperature, 0.17 g (2.1 mMol) of acetylchloride dissolved in 5 ml of dichloromethane are added dropwise thereto. The mixture is then refluxed for 1 hour, cooled, washed three times with 10 ml of water, dried with sodium sulphate and, after the drying agent has been filtered off in a rotary evaporator, finally at 80° C. under a full water jet vacuum, concentrated by evaporation. The residue is dissolved in 2 ml of methanol and after acidification with 2.5N ethanolic hydrochloric acid the solution is mixed with diethylether until just beginning to go cloudy. The crystals precipitated are suction filtered (after standing for about 12 hours in the refrigerator), washed with an ethanol/ether mixture (1:1), then with ether and dried at 80° C. The title compound is obtained in a yield of 0.49 g (68.8% of theory) with a melting point of 252° C. (decomp.) and a specific rotation of $[\alpha]_D^{25}=-108.2°$ (c=1, $CH_3OH$).

4.3.14 Example 86

(+)-(1S,5R,2"S)-2'-acetamido-2-(2-methoxypropyl)-5,9,9-trimethyl-6,7-benzomorphan hydrochloride Starting from 1.07 g (2.58 mMol) of (+)-(1S,5R,2"S)-2-amino-2-(2-methoxypropyl)-5,9,9-trimethyl-6,7-benzomorphan hydrochloride (Example 36) the title compound is obtained analogously to Example 85 in a yield of 0.73 g (74.3% of theory) with a melting point of 249° C. (decomp) and a specific rotation of $[\alpha]_D^{25}=-109.5°$ (c=1, $CH_3OH$).

4.3.15 Example 87

(−)-(1R,5S,2"S)-2'-acetamido-2-(2-methoxypropyl)-5,9,9-trimethyl-6,7-benzomorphan 1.09 g (0.0026 mol) of (−)-(1R,5S,2"S)-2'-amino-2-(2-methoxypropyl)-5,9,9-trimethyl-6,7-benzomorphan dihydrochloride are reacted analogously to Example 85. The reaction product is isolated as described therein and crystallised from 0.5 ml of isopropanol and 5 ml of petroleum ether. The title compound is obtained in a yield of 0.7 g (76.4% of theory) with a melting point of 128° C. and a specific rotation of $[\alpha]_D^{25}=-89.3°$ (c=1, $CH_3OH$-1N $HCl_{1:1}$).

4.3.16 Example 88

(+)-(1S,5R,2"R)-2'-acetamido-2-(2-methoxypropyl)-5,9,9-trimethyl-6,7-benzomorphan Starting from 1.11 g (2.5 mMol) of (+)-(1S,5R,2"R)-2'-amino-2(2methoxypropyl)-5,9,9-trimethyl-6,7-benzomorphan dimethanesulphonate (Example 35), the title compound is obtained analogously to Example 87 in a yield of 0.37 g (47.7% of theory) with a melting point of 129° C. and a specific rotation of $[\alpha]_D^{25}=89.9°$ (c=1, $CH_3OH$-1N $HCl_{1:1}$).

4.3.17 Example 89

(−)-(1R,5S,2"R)-3'-bromo-2'-hydroxy-2-(2-methoxypropyl)-5,9,9-trimethyl-6,7-benzomorphan hydrochloride 0.85 g (2.5 mMol) of (−)-(1R,5S,2"R)-2'-hydroxy-2-(2-methoxypropyl)-5,9,9-trimethyl-6,7-benzomorphan hydrochloride (Example 1) are suspended in 30 ml of glacial acetic acid. 0.15 ml (0.47 g, 2.9 mMol) of bromine are added to the suspension with stirring at ambient temperature. After 2 hours' stirring the mixture is evaporated down in a rotary evaporator, finally at 80° C. under a total water jet vacuum. The residue is mixed with 25 ml of water and 25 ml of dichloromethane with ammonia in excess, with agitation. The aqueous phase separated off is extracted once more with 15 ml of dichloromethane, the combined extracts are washed with 15 ml of water, dried with sodium sulphate and, after the drying agent has been filtered off—as described above— concentrated by evaporation. The residue (1 g) is purified by chromatography over a column containing 250 g of silica gel analogously to Example 2, using a mixture of dichloromethane, methanol and conc. ammonia (90:10:0.5). The eluates containing the pure substance are evaporated down as above and the residue is crystallised as the hydrochloride analogously to Example 2. The title compound is obtained in a yield of 0.75 g (65.8% of theory) with a melting point of 245° C. (decomp.) and a specific rotation of $[\alpha]_D^{25}=-82.5°$ (c=1, $CH_3OH$).

4.3.18 Example 90

(+)-(1R,5R,2"R)-2'-hydroxy-1'-nitro-2-(2-methoxypropyl)-5,9,9-trimethyl-6,7-benzomorphan hydrochloride 0.85 g (2.5 mMol) of (−)-(1R,5S,2"R)-2'-hydroxy-2-(2-methoxypropyl)-5,9,9-trimethyl-6,7-benzomorphan hydrochloride are suspended in 30 ml of glacial acetic acid at 20° C. and 0.18 ml (0.25 g) of 65% nitric acid (2.6 mMol of $HNO_3$) are added with stirring. Within about 10 minutes a clear yellow solution is formed which turns brown after another 5 minutes and begins to turn cloudy as a crystalline compound is precipitated. After a reaction time of 1 hour in total the mixture is suction filtered and washed with a glacial acetic acid/diethylether mixture (1:1), then with ether and dried at 80° C. The crystals (0.35 g) are dissolved in a hot methanol/water mixture (17.5 ml +1.75 ml) and diethylether (40 ml) is added to the solution. After cooling in an ice bath the substance which crystallises out is suction filtered, washed with ether and dried at 80° C. The title compound is obtained in a yield of 0.32 g (33.3% of theory) with a melting point of >245° C. (with gradual brown coloration and decomposition); specific rotation $[\alpha]_D^{25}=+87.0°$ (c=1, CH$_3$OH)

4.3.19 Example 91

(−)-(1R,5S,2"R)-2'-hydroxy-2-(2-methoxy-propyl)-3'-nitro-5,9,9-trimethyl-6,7-benzomorphan hydrochloride The nitrogenation described in Example 90 produces from the starting compound ($R_f$=0.57) the 1'-nitro-derivative described above ($R_f$=0.45), the isomeric 3'-nitro-derivative ($R_f$=0.72) and the 1',3'-dinitro-derivative ($R_f$=0.10) (TLC: silica gel 60, chloroform/methanol/conc. ammonia 90:10:0.5). The mother liquor remaining (Example 90) after the suction filtering of the 1'-nitro compound is evaporated down and the residue is converted into the free bases. These are dissolved in 10 ml of dichloromethane and the yellow solution is filtered over 25 g of aluminium oxide (activity III, neutral). The solution is eluted with dichloromethane until the eluate is no longer a strong yellow colour and the eluate is then evaporated down. The residue (0.35 g) is dissolved in 2.5 ml of ethanol and, after acidification with ethanolic hydrochloric acid, diethylether is added to the solution until it is just beginning to turn cloudy. After it has stood for about 12 hours in the refrigerator it is suction filtered, washed with an ethanol/ether mixture (1:1) and dried at a temperature of 80° C. The title compound is obtained in a yield of 0.40 g (41.6% of theory) with a melting point of 229°–230° C. (decomp.) and a specific rotation of $[\alpha]_D^{25}=-110.1°$ (c=1, CH$_3$OH).

4.3.20 Example 92

(+)-(1R,5R,2"R)-2',3'-dinitro-2'-hydroxy-2-(2-methoxypropyl)-5,9,9-trimethyl-6,7-benzomorphan hydrochloride 1.52 g (5 mMol) of (−)-(1R,5S,2"R)-2'-hydroxy-2-(2-methoxypropyl)-5,9,9-trimethyl-6,7-benzomorphan (Example 1) are dissolved in 3 ml of glacial acetic acid and, whilst stirring at 3°–4° C., a mixture of 3.4 ml of glacial acetic acid and 5.42 ml of 100% nitric acid are added to the solution within 1.5 hours. The resulting mixture is stirred for a further 3 hours at ambient temperature. Then the yellow reaction mixture is poured into 50 g of ice water, the solution is made ammoniacal and extracted three times with 20 ml of dichloromethane. After the combined extracts have been washed with water and dried over sodium sulphate and the drying agent has been filtered off, the reaction mixture is evaporated down in a rotary evaporator, finally at 80° C. under a total water jet vacuum. The residue is crystallised from an ethanol/ether mixture. The title compound is obtained in a yield of 1.0 g (46.5% of theory) with a melting point of >300° C. (decomp.) and a specific rotation of $[\alpha]_D^{25}=+27.9°$ (c=1, CH$_3$OH).

4.3.21 Example 93

(−)-(1R,5R,2"R)-1'-amino-2'-hydroxy-2-(2-methoxypropyl)-5,9,9-trimethyl-6,7-benzomorphan hydrochloride 0.35 g (1.0 mMol) of (+)-(1R,5R,2"R)-2'-hydroxy-2-(2-methoxypropyl)-1'-nitro-6,7-benzomorphan hydrochloride (Example 90) are hydrogenated in 40 ml of methanol in the presence of 0.1 g of palladium/charcoal (5% Pd) for 4 hours under a hydrogen pressure of 5 bar at ambient temperature. After the catalyst has been filtered off the reaction mixture is evaporated down in a rotary evaporator, finally at 80° C. under a total water jet vacuum and the residue is crystallised from 10 ml of ethanol. After cooling in an ice bath the crystals are suction filtered, washed with an ethanol/ether mixture and dried at 80° C. The title compound is obtained in a yield of 0.17 g (52.7% of theory) with a melting point of 282° C. (after slow decomposition from 250° C.) and a specific rotation of $[\alpha]_D^{25}=-128.3°$ (c=1, CH$_3$OH).

4.3.22 Example 94

(−)-(1R,5S,2"R)-3'-amino-2'-hydroxy-2-(2-methoxypropyl)-5,9,9-trimethyl-6,7-benzomorphan hydrochloride Starting from 0.39 g (1.0 mMol) of (−)-(1R,5S,2"R)-2'-hydroxy-2-(2-methoxypropyl)-3'-nitro-5,9,9-trimethyl-6,7-benzomorphan hydrochloride (Example 91) the title compound is obtained analogously to Example 93 in a yield of 0.27 g (76.1% of theory) with a melting point of 268° C. (decomp.) and a specific rotation of $[\alpha]_D^{25}=-99.7°$ (c=0.5, CH$_3$OH).

4.3.23 Example 95

(−)-(1R,5R,2"R)-1',3'-diamino-2'-hydroxy-2-(2-methoxypropyl)-5,9,9-trimethyl-6,7-benzomorphan hydrochloride Starting from 0.70 g (1.63 mMol) of (+)-(1R,5R,2"R)-1',3'-dinitro-2'-hydroxy-2-(2-methoxy-propyl)-5,9,9-trimethyl-6,7-benzomorphan hydrochloride (Example 92) the title compound is obtained analogously to Example 93 in a yield of 0.20 g (33.2% of theory) with a melting point of 228° C. (decomp.) and a specific rotation of $[\alpha]_D^{25}=-111.7°$ (c=0.5, CH$_3$OH).

4.3.24 Example 96

(−)-(1R,5S,2"R)-3'-amino-2-(2-methoxypropyl)-5,9,9-trimethyl-6,7-benzomorphan

The diastereomixture obtained according to Example 67 consisting of (−)-(1R,5S,2"R)- and (+)-(1S,5R,2"R)-2-(2-methoxypropyl)-3'-nitro-5,9,9-trimethyl-6,7-benzomorphan (3.7 g) is dissolved in 75 ml of methanol and hydrogenated in the presence of 0.8 g of palladium/charcoal (5% Pd) under a hydrogen pressure of 5 bar and a temperature of 20° C. until the uptake of hydrogen ceases (about 3 hours). In thin layer chromatography (silica gel 60, chloroform/methanol/conc. ammonia 90:10:0.5) it is found that the 3'-nitro compounds ($R_f$=0.73) have reacted completely to form the corresponding 3'-amino-compounds ($R_f$=0.61). After the catalyst has been filtered off the reaction mixture is evaporated down in a rotary evaporator, finally at 80° C. under a total water jet vacuum. The residue (3.1 g) is subjected to column chromatography on 600 g of silica gel analogously to Example 2. The separation of the diastereomeric 3'-amino-compounds is monitored by thin layer chromatography (silica gel 60, chloroform/methanol/conc. ammonia 95:5:0.1, developed twice). The title compound with the smaller $R_f$ value of 0.63 is obtained in a yield of 0.95 g as the evaporation residue of the corresponding eluates with a specific rotation of $[\alpha]_D^{25}=-39.8°$ (c=1, CH$_3$OH) which has hitherto resisted all attempts at crystallisation.

4.3.25 Example 97

(+)-(1S,5R,2"R)-3'-amino-2-(2-methoxypropyl)-5,9,9-trimethyl-6,7-benzomorphan

In the separation of the diastereomers by column chromatography described above (Example 96) the substance

4.3.26 Example 98

(+)-(1S,5R,2"S)-3'-amino-2-(2-methoxypropyl)-5,9,
9-trimethyl-6,7-benzomorphan a) 3'-nitro-precursor (mixture of diastereomers)

Starting from 5.2 g (0.02 mol) of (±)-3'-nitro-5,9,9-trimethyl-6,7-benzomorphan and 5.36 g (0.022 mol) of (S)-2-methoxypropyl-p-toluene-sulphonate and a mixture of the two expected diastereomeric bases is obtained analogously to Example 67 and is purified by filtration over aluminium oxide, resulting in 4.7 g of purified base mixture.

b) 3'-amino-compounds (mixture of diastereomers)

The 3'-nitro-precursor (4.7 g of purified mixture of diastereomers) is hydrogenated analogously to Example 96 to form the corresponding 3'-amino compounds (3.7 g of mixture of diastereomers).

c) Separation of the title compound by column chromatography

The mixture of diastereomeric 3'-amino-compounds (3.7 g) is separated by column chromatography on silica gel analogously to Example 96. The title compound with the smaller $R_f$ value of 0.63 is obtained in a yield of 1.0 g as the evaporation residue of the eluates in question with a specific rotation of $[\alpha]_D^{25}=+40.5°$ (c=1, CHOH), which has hitherto withstood all attempts at crystallisation.

4.3.27 Example 99

(−)-(1R,5S,2"S)-3'-amino-2-(2-methoxypropyl)-5,9,
9-trimethyl-6,7-benzomorphan

In the column chromatography described above (Example 98) the title compound is obtained as the second substance with the greater $R_f$ value of 0.69, in the form of the evaporation residue of the eluates in question in a quantity of 1.1 g, specific rotation: $[\alpha]_D^{25}=-105°$ (c=1, CH$_3$OH), and has not hitherto crystallised.

4.3.28 Example 100

(−)-(1R,5S,2"R)-3'-acetamido-2-(2-methoxypropyl)-
5,9,9-trimethyl-6,7-benzomorphan 0.95 g (3.14 mMol) of (−)-(1R,5S,2"R)-3'-amino-2-(2-methoxypropyl)-5,9,9-trimethyl-6,7-benzomorphan (Example 96) are acetylated analogously to Example 85. The acetylation product is purified by filtration over aluminium oxide analogously to Example 65. In thin layer chromatography (silica gel 60, chloroform/methanol/conc. ammonia 90:10:0.5) the starting compound has an $R_f$ value of 0.64 and the acetylation product has an $R_f$ value of 0.57. The evaporation residue (0.69 g), which has hitherto resisted all attempts at crystallisation, has a specific rotation of $[\alpha]_D^{25}=-53.6°$ (c=1, CH$_3$OH)

4.3.29 Example 101

(+)-(1S,5R,2"R)-3'-acetamido-2-(2-methoxypropyl)-
5,9,9-trimethyl-6,7-benzomorphan oxalate Starting from 1.0 g (3.31 mMol) of (+)-(1S,5R,2"R)-3'-amino-2-(2-methoxypropyl)-5,9,9-trimethyl-6,7-benzomorphan (Example 97) the title compound is obtained analogously to Example 100. The evaporation residue of the substance purified over aluminium oxide (0.5 g) is crystallised in the form of the oxalate analogously to Example 83. The title compound is obtained in a yield of 0.4 g (27.8% of theory) with a melting point of 148° C. (decomp.) and a specific rotation of $[\alpha]_D^{25}=+39.3°$ (c=1, CH$_3$OH).

4.3.30 Example 102

(+)-(1S,5R,2"S)-3'-acetamido-2-(2-methoxypropyl)-
5,9,9-trimethyl-6,7-benzomorphan Starting from 1.0 g (3.31 mMol) of (+)-(1S,5R,2"S)-3'-amino-2-(2-methoxypropyl)-5,9,9-trimethyl-6,7-benzomorphan (Example 98) the title compound is obtained analogously to Example 100 as a noncrystallising evaporation residue (0.6 g, 41.7% of theory) with an $R_f$ value of 0.57 and a rotation of $[\alpha]_D^{25}=+52.8°$ (c=1, CH$_3$OH).

4.3.31 Example 103

(−)-(1R,5S,2"S)-3'-acetamido-2-(2-methoxypropyl)-
5,9,9-trimethyl-6,7-benzomorphan oxalate Starting from 0.95 g (3.14 mMol) of (−)-(1R,5S,2"S)-3'-amino-2-(2-methoxypropyl)-5,9,9-trimethyl-6,7-benzomorphan (Example 99) the title compound is obtained analogously to Example 101 in a yield of 0.7 g (51.1%) with a melting point of 148° C. (decomp.) and a specific rotation of $[\alpha]_D^{25}=-39.2°$ (c=1, CH$_3$OH)

4.3.32 Example 104

(−)-(1R,5S,2"R)-3'-methoxy-2-(2-methoxy-propyl)-
5,9,9,2'-tetramethyl-6,7-benzomorphan
hydrochloride Starting from 0.71 g (2 mMol) of (−)-(1R,5S,2"R)-3'-hydroxy-2-(2-methoxypropyl)-5,9,9,2'-tetramethyl-6,7-benzomorphan hydrochloride (Example 53) the title compound is obtained analogously to Example 73 in a yield of 0.38 g (52.0%) with a melting point of 221°–224° C. and a specific rotation of $[\alpha]_D^{25}=-82.6°$ (c=1, CH$_3$OH).

4.3.33 Example 105

(+)-(1S,5R,2"R)-3'-methoxy-2-(2-methoxy-propyl)-
5,9,9,2'-tetramethyl-6,7-benzomorphan
hydrochloride Starting from 0.71 g (2 mMol) of (+)-(1S,5R,2"R)-3'-hydroxy-2-(2-methoxypropyl)-5,9,9,2'-tetramethyl-6,7-benzomorphan hydrochloride (Example 54) the title compound is obtained analogously to Example 73 in a yield of 0.44 g (59.8%) as an amorphous powder with a specific rotation of $[\alpha]_D^{25}=+42.2°$ (c=1, CH$_3$OH).

4.3.34 Example 106

(+)-(1S,5R,2"S)-3'-methoxy-2-(2-methoxy-propyl)-
5,9,9,2'-tetramethyl-6,7-benzomorphan
hydrochloride Starting from 0.71 g (2 mMol) of (+)-(1S,5R,2"S)-3'-hydroxy-2-(2-methoxypropyl)-5,9,9,2'-tetramethyl-6,7-benzomorphan hydrochloride (Example 55) the title compound is obtained analogously to Example 73 in a yield of 0.40 g (54.7%) with a melting point of 221°–224° C. and a specific rotation of $[\alpha]_D^{25}=+81.7°$ (c=1, CH$_3$OH).

4.3.35 Example 107

(−)-(1R,5S,2"S)-3'-methoxy-2-(2-methoxy-propyl)-
5,9,9,2'-tetramethyl-6,7-benzomorphan
hydrochloride Starting from 0.71 g (2 mMol) of (−)-(1R,5S,2"S)-3'-hydroxy-2-(2-methoxypropyl)-5,9,9,2'-tetramethyl-6,7-

4.3.36 Example 108

(−)-(1R,5S,2"R)-2'-methoxy-2-(2-methoxy-propyl)-5,9,9,3'-tetramethyl-6,7-benzomorphan hydrochloride Starting from 0.71 g (2 mMol) of (−)-(1R,5S,2"R)-2'-hydroxy-2-(2-methoxypropyl)-5,9,9,3'-tetramethyl-6,7-benzomorphan hydrochloride (Example 57) the title compound is obtained analogously to Example 73 in a yield of 0.36 g (49.3%) with a melting point of 221°–224° C. and a specific rotation of $[\alpha]_D^{25}=-112.2°$ (c=1, CH$_3$OH).

4.3.37 Example 109

(+)-(1S,5R,2"R)-2'-methoxy-2-(2-methoxy-propyl)-5,9,9,3'-tetramethyl-6,7-benzomorphan hydrochloride Starting from 0.71 g (2 mMol) of (+)-(1S,5R,2"R)-2'-hydroxy-2-(2-methoxypropyl)-5,9,9,3'-tetramethyl-6,7-benzomorphan hydrochloride (Example 58) the title compound is obtained analogously to Example 73 in a yield of 0.39 g (53.0%) as an amorphous powder with a specific rotation of $[\alpha]_D^{25}=+72.4°$ (c=1, CH$_3$OH).

4.3.38 Example 110

(+)-(1S,5R,2"S)-2'-methoxy-2-(2-methoxy-propyl)-5,9,9,3'-tetramethyl-6,7-benzomorphan hydrochloride Starting from 0.64 g (2 mMol) of (+)-(1S,5R,2"S)-2'-hydroxy-2-(2-methoxypropyl)-5,9,9,3'-tetramethyl-6,7-benzomorphan hydrochloride (Example 59) the title compound is obtained analogously to Example 73 in a yield of 0.45 g (61.5%) with a melting point of 228°–229° C. and a specific rotation of $[\alpha]_D^{25}=+111.5°$ (c=1CH$_3$OH).

4.3.39 Example 111

(−)-(1R,5S,2"S)-2'-methoxy-2-(2-methoxy-propyl)-5,9,9,3'-tetramethyl-6,7-benzomorphan hydrochloride Starting from 0.71 g (2 mMol) of (−)-(1R,5S,2"S)-2'-hydroxy-2-(2-methoxypropyl)-5,9,9,3'-tetramethyl-6,7-benzomorphan hydrochloride (Example 60) the title compound is obtained analogously to Example 73 in a yield of 0.40 g (53.4%) as an amorphous powder with a specific rotation of $[\alpha]_D^{25}=-71.8°$ (c=1, CH$_3$OH).

4.3.40 Example 112

(−)-(1R,5S,2"R)-3'-hydroxy-2'-methoxy-2-(2-methoxypropyl)-5,9,9-trimethyl-6,7-benzomorphan hydrobromide Starting from 3.56 g (10 mMol) of (−)-(1R,5S,2"R)-2',3'-dihydroxy-2-(2-methoxypropyl)-5,9,9-trimethyl-6,7-benzomorphan hydrochloride (Example 61) a mixture of the two isomeric monomethoxy derivatives and the dimethoxy derivative is obtained analogously to Example 73, except with two equivalents of sodium hydride, and this mixture is separated by column chromatography on 100 times the quantity of silica gel analogously to Example 2 [eluant: dichloromethane/isopropanol/conc. ammonia 97:3:03]. The compound which runs out as the middle substance (R$_f$=0.73) is crystallised as the hydrobromide. The title compound is obtained in a yield of 0.62 g (15.0%) with a melting point of 212° C. (decomp.) and a specific rotation of $[\alpha]_D^{25}=-78.4°$ (c=0.5; CH$_3$OH).

4.3.41 Example 113

(−)-(1R,5S,2"R)-2'-hydroxy-3'-methoxy-2-(2-methoxypropyl)-5,9,9-trimethyl-6,7-benzomorphan hydrobromide The slower running substance (R$_f$=0.68) separated off in Example 112 is precipitated as the hydrobromide. The title compound is obtained in a yield of 0.88 g (21.2%) with a melting point of 235° C. (decomp.) and with a specific rotation of $[\alpha]_D^{25}=-93.1°$ (c=0.5; CH$_3$OH).

4.3.42 Example 114

(−)-(1R,5S,2"R)-2',3'-dimethoxy-2-(2-methoxypropyl)-5,9,9-trimethyl-6,7-benzomorphan hydrochloride The faster running substance (R$_f$=0.86) separated off in Example 112 is precipitated as the hydrochloride. The title compound is obtained in a yield of 0.87 g (22.7%) with a melting point of 193° C. (decomp.) and a specific rotation of $[\alpha]_D^{25}=-93.2°$ (c=0.5; CH$_3$OH).4.4 Compounds (1) by special methods

4.4.1 Example 115

(−)-(1R,5S,2"R)-2'-hydroxy-2-(2-hydroxy-propyl)-5,9,9-trimethyl-6,7-benzomorphan hydrochloride 1.5 g (3.60 mMol) of (−)-(1R,5S,2"R)-2-(2-benzyloxypropyl)-2'-hydroxy-5,9,9-trimethyl-6,7-benzomorphan hydrochloride (Example 43) are dissolved in 75 ml of methanol and hydrogenated in the presence of palladium hydroxide on activated charcoal (0.6 g of moist "Pearlman catalyst") under a hydrogen pressure of 5 bar and at a temperature of 70° C. until completely reacted (about 6.2 hours). Then the catalyst is filtered off and the filtrate is evaporated down in a rotary evaporator, finally at 80° C. under a total water jet vacuum. The residue is dissolved in 10 ml of methanol and 30 ml of diethylether are added to the solution. The crystals precipitated are left to stand for about 12 hours at ambient temperature, then suction filtered, first with an ethanol/ether mixture (1:1), then with ether, and dried at 80° C. The title compound is obtained in a yield of 1.0 g (85.5% of theory) with a melting point of 276° (decomp.) and a specific rotation of $[\alpha]_D^{25}=-127.4°$ (c=1, CH$_3$OH)

4.4.2 Example 116

(+)-(1S,5R,2"S)-2'-hydroxy-2-(2-hydroxy-propyl)-5,9,9-trimethyl-6,7-benzomorphan hydrochloride Starting from 1.5 g (3.6 mMol) of (+)-(1S,5R,2"S)-2-(2-benzyloxypropyl)-2'-hydroxy-5,9,9-trimethyl-6,7-benzomorphan hydrochloride (Example 44) the title compound is obtained analogously to Example 115 in a yield of 1.0 g (85.5% of theory) with a melting point of 276° (decomp.) and a specific rotation of $[\alpha]_D^{25}=+126.8°$ (c=1, CH$_3$OH)

4.4.3 Example 117

(−)-(1R,5S,2"S)-2'-hydroxy-2-(2-hydroxy-propyl)-5,9-trimethyl-6,7-benzomorphan hydrochloride The diastereomer remaining in the mother liquor according to Example 44 (3.17 g of evaporation residue) is hydrogenated analogously to Example 115. The title compound is obtained in a yield of 1.5 g (56.2% of theory) with a melting point of 247° C. (decomp.) and a specific rotation of $[\alpha]_D^{25}=-86.8°$ (c=1, $CH_3OH$).

4.4.4 Example 118

(+)-(1S,5R,2"R)-2'-hydroxy-2-(2-hydroxy-propyl)-5,9,9-trimethyl-6,7-benzomorphan hydrochloride The diastereomer remaining in the mother liquor according to Example 43 (3.17 g of evaporation residue) is hydrogenated analogously to Example 115. The title compound is obtained in a yield of 1.5 g (56.2% of theory) with a melting point of 247° C. (decomp.) and a specific rotation of $[\alpha]_D^{25}=+86.4°$ (c=1, $CH_3OH$).

4.4.5 Example 119

(+)-(1R/S,5S/R,2"S)-2'-fluoro-2-(2-methoxypropyl)-5,9,9-trimethyl-6,7-benzomorphan oxlate a) Starting compound: (1R/S,5S/R,2"S)-2'-fluoro-2-(2-methoxypropionyl)-5,9,9-trimethyl-6,7-benzomorphan (mixture of diastereomers)

5.94 g (0.02 mol) of (±)-2'-nitro-5,9,9-trimethyl-6,7-benzomorphan hydrochloride are acylated analogously to Example 32 with 2.68 g (0.22 mol) of (S)-2-methoxypropionic acid chloride. The acylation product thus obtained (7.0 g) is hydrogenated as described therein to form the corresponding 2'-amino-analogue. This latter is reacted, using methods known from the prior art [T. L. Fletcher and M. J. Namkung, Chem. and Ind. 1961, 179] to form the corresponding. 2'-fluoro derivative (5.7 g). This results in a mixture of the expected diastereomers, which cannot be separated by thin layer chromatography ($R_f$=0.73, silica gel, chloroform/methanol/conc. ammonia 90:10:0.5).

b) Reaction to obtain the title compound 1.58 g (5 mMol) of the precursor are reduced with lithium aluminium hydride ($LiAlH_4$) to form the title compound analogously to Example 32 and purified by column chromatography on silica gel as described therein. The evaporation residue of the eluates with the purified substance (0.4 g, $R_f$=0.78) is crystallised as the oxalate analogously to Example 83. The title compound is obtained in a yield of 0.35 g (17.7% of theory) with a melting point of 165° C. (decomp.) and with a rotation of $[\alpha]_D^{25}=+9.7°$ (c=1, $CH_3OH$). The substance consists of a mixture of the expected diastereomers ((1R,5S,2"S)- and (1S,5R2"S)-compound) in a ratio of about 1:1 (determined by $^1H$-NMR spectroscopy).

4.4.6 Example 120

(−)-(1R/S,5S/R,2"R)-2'-fluoro-2-(2-methoxypropyl)-5,9,9-trimethyl-6,7-benzomorphan oxalate a) Starting compound: (1R/S,5S/R,2"R)-2"fluoro-2-(2-methoxypropionyl)-5,9,9-trimethyl-6,7-benzomorphan (mixture of diastereomers)

Starting from 2.97 g (0.01 mol) of (±)-2'-nitro-5,9,9-trimethyl-6,7-benzomorphan hydrochloride, a mixture of the expected diastereomeric 2'-fluoro-2-(2-methoxypropionyl)-5,9,9-trimethyl-6,7-benzomorphans is obtained, using 1.34 g (0.011 mol) of (R)-2-methoxy-propionic acid chloride (reaction sequence as in Example 119). These diastereomers cannot be separated by thin layer, chromatography ($R_f$=0.73, silica gel, chloroform/methanol/conc. ammonia 90:10:0.5), yield: 2.9 g.

b) Reaction to form the title compound 2.9 g (9.2 mMol) of the above precursor are reduced with lithium aluminium hydride analogously to Example 119 to obtain the title compound. The reaction is purified as described therein. The evaporation residue of the pure fractions (0.9 g) is crystallised as the oxalate analogously to Example 98. The title compound is obtained in a yield of 0.88 g (22.3% of theory) with a melting point of 169° C. (decomp.) and a specific rotation of $[\alpha]_D^{25}=-9.5°$ (c=1, $CH_3OH$) in the form of a mixture of the expected diastereomers ((1R,5S,2"R)- and (1S,5R,2"R)-compounds).

What is claimed is:

1. A benzomorphan derivative of formula I

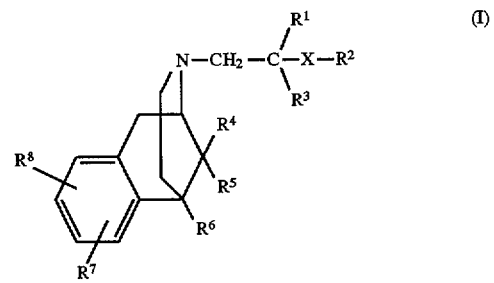

wherein

X is oxygen or sulphur;

$R^1$ is $C_{1-8}$-alkyl, $C_{3-6}$-alkenyl, $C_{3-6}$-alkynyl, an aromatic group having 6 to 10 carbon atoms, also in combinations, it being possible for the aromatic moiety to be substituted by one or more lower alkyl groups, alkoxy groups, nitro groups, amino groups or one or more halogen atoms which may be identical to or different from one another;

is hydrogen, $C_{1-8}$-alkyl, $C_{3-6}$-alkenyl, $C_{3-6}$-alkynyl, an aromatic group having 6 to 10 carbon atoms, also in combinations, it being possible for the aromatic moiety to be substituted by one or more lower alkyl groups, alkoxy groups, nitro groups, amino groups or one or more halogen atoms which may be identical to or different from one another;

an aryl group bound to an alkylene chain and having 7 to 14 carbon atoms, whilst the aromatic moiety may be substituted with one or more lower alkyl groups, alkoxy groups, nitro groups, amino groups or one or more halogen atoms, which may be identical to or different from one another;

$R^3$ is hydrogen or $C_{1-6}$-alkyl;

$R^4$ is $C_{1-8}$-alkyl;

$R^5$ is $C_{1-8}$-alkyl;

$R^6$ is $C_{1-8}$-alkyl, an aromatic group having 6 to 10 carbon atoms, also in combinations, it being possible for the aromatic moiety to be substituted by one or more lower alkyl groups, alkoxy groups, nitro groups, amino groups or one or more halogen atoms which may be identical to or different from one another;

$R^7$ and $R^8$, independently of each other, are hydrogen, $C_{1-8}$-alkyl, halogen, —OH, $C_{1-8}$-alkoxy, an O-benzoyl or O-alkyl carbonyl group with one straight-chained or branched lower alkyl group having 1 to 6 carbon atoms, wherein the alkyl group may optionally be substituted with one or more halogen atoms which may be identical to or different from one another, —CN, —$NO_2$, -$NH_2$, —NH($C_{1-8}$-alkyl), —N($C_{1-8}$-alkyl)$_2$, wherein the alkyl groups may be identical or different, —NH-acyl or —N-acyl-($C_{1-8}$-alkyl), wherein acyl is benzoyl or an alkyl carbonyl group with a straight-chained or branched lower alkyl group having 1 to 6 carbon atoms, whilst the alkyl group may optionally be substituted with one or more halogen atoms which may be identical to or different from one another, the stereoisomers thereof as well as the pharmaceutically acceptable acid addition salts thereof, with the proviso that if X is oxygen;

$R^1$ is $C_{1-3}$-alkyl, $C_3$-alkenyl, or $C_3$-alkynyl;

$R^2$ is hydrogen, $C_{1-4}$-alkyl, $C_3$-or $C_4$-alkenyl;

$R^3$ is hydrogen or $C_{1-3}$-alkyl;

$R^4$ is methyl;

$R^5$ is methyl;

$R^6$ is $C_{1-4}$-alkyl or phenyl and one of the two substituents $R^7$ or $R^8$ is hydrogen, the remaining substituent $R^7$ or $R^8$ in the 2'-position must not be hydrogen, hydroxy, $C_{1-3}$-alkoxy or O-alkyl carbonyl.

2. The benzomorphan derivative as recited in claim 1 wherein

X is oxygen or sulphur;

$R^1$ is methyl, ethyl, propyl, isopropyl, phenyl;

$R^2$ is methyl, ethyl, propyl, isopropyl, allyl, propargyl, phenyl, benzyl;

$R^3$ is hydrogen or $C_{1-4}$-alkyl;

$R^4$ is methyl, ethyl, propyl, isopropyl;

$R^5$ is methyl, ethyl, propyl, isopropyl;

$R^6$ is methyl, ethyl, propyl, isopropyl, phenyl;

$R^7$ is fluorine, chlorine, hydroxy, lower alkyl, $C_{1-3}$-alkoxy, an O-benzoyl or O-alkyl carbonyl group with one straight-chained or branched lower alkyl group having 1 to 6 carbon atoms, wherein the alkyl group may optionally be substituted with one or more halogen atoms which may be identical to or different from one another;

$R^8$ is hydrogen, lower alkyl, hydroxy or $C_{1-3}$-alkoxy the stereoisomers and pharmaceutically acceptable acid addition salts thereof.

3. The benzomorphan derivative as recited in claim 1 wherein

X is oxygen;

$R^1$ is methyl, ethyl;

$R^2$ is methyl, ethyl;

$R^3$ is hydrogen;

$R^4$ is methyl, ethyl;

$R^5$ is methyl, ethyl;

$R^6$ is methyl, ethyl;

$R^7$ is hydroxy, methyl, methoxy, an O-benzoyl or O-alkyl carbonyl group with one straight-chained or branched lower alkyl group having 1 to 6 carbon atoms, wherein the alkyl group may optionally be substituted with one or more halogen atoms which may be identical to or different from one another;

$R^8$ is hydrogen, methyl, ethyl, hydroxy or $C_{1-3}$-alkoxy the stereoisomers and pharmaceutically acceptable acid addition salts thereof.

4. The benzomorphan derivative as recited in claim 1 wherein

X is oxygen;

$R^1$ is methyl;

$R^2$ is methyl;

$R^3$ is hydrogen;

$R^4$ is methyl;

$R^5$ is methyl;

$R^6$ is methyl;

$R^7$ is hydroxy, methyl, methoxy, acetoxy;

$R^8$ is hydrogen, methyl, hydroxy or $C_{1-3}$-alkoxy the stereoisomers and pharmaceutically acceptable acid addition salts thereof.

5. The benzomorphan derivative as recited in claim 1 wherein

X is oxygen;

$R^1$ is methyl;

$R^2$ is methyl;

$R^3$ is hydrogen;

$R^4$ is methyl;

$R^5$ is methyl;

$R^6$ is methyl;

$R^7$ is hydroxy, methyl, methoxy, acetoxy;

$R^8$ is hydrogen, methyl, hydroxy, methoxy or ethoxy, where $R^7$ is in the 3'-position and $R^8$ is in the 2'-position and the 2"-carbon atom has the R-configuration, as well as the pharmaceutically acceptable acid addition salts thereof.

* * * * *